(12) United States Patent
Lee et al.

(10) Patent No.: US 10,683,282 B2
(45) Date of Patent: Jun. 16, 2020

(54) MULTI-SUBSTITUTED PYRIMIDINE DERIVATIVES WITH EXCELLENT KINASE INHIBITORY ACTIVITIES

(71) Applicant: KOREA INSTITUTE OF SCIENCE AND TECHNOLOGY, Seoul (KR)

(72) Inventors: So Ha Lee, Seoul (KR); Kyung Ho Yoo, Seoul (KR); Eun Joo Roh, Seoul (KR); Tae Bo Sim, Seoul (KR); Tae Young Kim, Seoul (KR); Jae Ho Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/362,571

(22) Filed: Mar. 22, 2019

(65) Prior Publication Data

US 2019/0315726 A1 Oct. 17, 2019

(30) Foreign Application Priority Data

Apr. 11, 2018 (KR) ........................ 10-2018-0042031

(51) Int. Cl.
| | | |
|---|---|---|
| *C07D 405/14* | (2006.01) | |
| *C07D 405/12* | (2006.01) | |
| *C07D 403/12* | (2006.01) | |
| *C07D 401/12* | (2006.01) | |
| *C07D 239/48* | (2006.01) | |
| *A61P 35/00* | (2006.01) | |
| *A61P 25/28* | (2006.01) | |
| *A61P 37/02* | (2006.01) | |
| *A61P 29/00* | (2006.01) | |

(52) U.S. Cl.
CPC ............ *C07D 405/14* (2013.01); *A61P 25/28* (2018.01); *A61P 29/00* (2018.01); *A61P 35/00* (2018.01); *A61P 37/02* (2018.01); *C07D 239/48* (2013.01); *C07D 401/12* (2013.01); *C07D 403/12* (2013.01); *C07D 405/12* (2013.01)

(58) Field of Classification Search
CPC .. C07D 405/12; C07D 239/48; C07D 405/14; C07D 403/12; C07D 401/12; A61P 35/00; A61P 25/28; A61P 29/00; A61P 37/02
See application file for complete search history.

(56) References Cited

U.S. PATENT DOCUMENTS

2006/0247262 A1 11/2006 Baenteli et al.

FOREIGN PATENT DOCUMENTS

| KR | 10-2014-0097496 A | 8/2014 |
|---|---|---|
| KR | 10-2017-0027757 A | 3/2017 |
| KR | 10-2018-0073682 A | 7/2018 |
| KR | 10-1916773 B1 | 11/2018 |
| KR | 1916773 * | 11/2018 |
| WO | 03-055866 A1 | 7/2003 |
| WO | 2005-026130 A1 | 3/2005 |
| WO | 2006-101977 A2 | 9/2006 |
| WO | 2007-053452 A1 | 5/2007 |
| WO | 2008-115742 A1 | 9/2008 |
| WO | 2009-046416 A1 | 4/2009 |
| WO | 2015-123453 A1 | 8/2015 |

OTHER PUBLICATIONS

CAS Abstract KR 1916773 (2018).*
Hai-Yan Zhang et al. Activation of ARK5/miR-1181/HOXA10 axis promotes epithelial-mesenchymal transition in ovarian cancer, Oncology Report 34, Apr. 3, 2015, pp. 1193-1202.
Peng Chen et al. High NUAK1 expression correlates with poor prognosis and involved in NSCLC cells migration and invasion, Experimental Lung Research, 2013, pp. 9-17,vol. 39.
Abdelhamid Bekri et al. Analysis of NUAK1 and NUAK2 expression during early chick development reveals specific patterns in the developing head, Int. J. Dev. Biol. 58, Sep. 30, 2014, pp. 379-384.
Cristian A. Lasagna-Reeves et al, Reduction of Nuak1 Decreases Tau and Reverses Phenotypes in aTauopathy Mouse Model , Neuron 92, Oct. 19, 2016, pp. 407-418.
Xinyan Wu et al. The non-receptor tyrosine kinase TNK2/ACK1 is a novel therapeutic target in triple negative breast cancer, Oncotarget, Nov. 25, 2016, pp. 2971-2983, vol. 8(No. 2).
Daniella M. Schwartz1 et al. JAK inhibition as a therapeutic strategy for immune and inflammatory diseases, Nature Reviews Drug Discovery, Dec. 28, 2017, pp. 843-862, vol. 16.

* cited by examiner

*Primary Examiner* — Alexander R Pagano
*Assistant Examiner* — Ebenezer O Sackey
(74) *Attorney, Agent, or Firm* — Goldilocks Zone IP Law

(57) ABSTRACT

Disclosed are a novel pyrimidine derivative compound, a pharmaceutically acceptable salt thereof, a method for preparing the compound and a pharmaceutical use of the compound as an anticancer agent or a therapeutic agent for degenerative brain diseases. Specifically, the novel pyrimidine derivative compound has excellent inhibitory activities against kinase enzymes such as ARK5/NUAK1, ACK1, FLT3, JAK1, JAK2 and JAK2 (V617F) and thus is useful for treating and preventing leukemia, ovarian cancer, breast cancer, non-small cell carcinoma, colorectal cancer, glioma, and brain protein abnormalities such as Alzheimer's disease, progressive supranuclear palsy and frontotemporal dementia, that is, degenerative diseases caused by Tau deposition.

20 Claims, No Drawings

MULTI-SUBSTITUTED PYRIMIDINE DERIVATIVES WITH EXCELLENT KINASE INHIBITORY ACTIVITIES

CROSS-REFERENCE TO RELATED APPLICATION

This application claims, under 35 U.S.C. § 119(a), the benefit of priority to Korean Patent Application No. 10-2018-0042031 filed on Apr. 11, 2018, the entire contents of which are incorporated herein by reference.

BACKGROUND

(a) Technical Field

The present invention relates to a pyrimidine derivative compound having various substituents, a pharmaceutically acceptable salt thereof, a method for preparing the compound and a pharmaceutical use of the compound.

(b) Background Art

Protein kinases are enzymes that catalyze the phosphorylation of hydroxyl groups positioned in the tyrosine, serine and threonine residues of proteins and play a key role in the signaling of growth factors causing cell growth, differentiation and proliferation.

In order to maintain homeostasis of the living body, the balance between on and off in the in vivo signal transduction pathways should be smooth. However, mutation or overexpression of certain protein kinases disrupts normal intracellular signal transduction pathways (predominantly, continuation of in vivo signal transduction), leading to a variety of diseases including cancer, inflammation, metabolic diseases and brain diseases. Representative protein kinases that cause abnormal cell growth disorders include Raf, KDR, Fms, Tie2, SAPK2a, Ret, Abl, Abl(T315I), ALK, Aurora A, Bmx, CDK/cyclinE, Kit, Src, EGFR, EphAl, FGFR3, FLT3, IGF-1R, IKKb, IR, Itk, JAK2, KDR, Met, mTOR, PDGFRa, Plk1, Ret, Syk, Tie2, TrtB and the like. Therefore, research is underway to develop targeted anticancer drugs through development of compounds having selective inhibitory activities against specific kinases among various protein kinases.

PRIOR ART

Patent Document (Patent Document 1) PCT International Patent Publication WO 2005-026130 A1
(Patent Document 2) PCT International Patent Publication WO 2009-046416 A1
(Patent Document 3) PCT International Patent Publication WO 2007-053452 A1

Non-Patent Document (Non-Patent Document 1) Hai-Yan Zhang et al. Oncology Report, 2015, 34, 1193-1202
(Non-Patent Document 2) Peng Chen et al. Experimental Lung Research, 2013, 39, 9-17
(Non-Patent Document 3) Abdelhamid Bekri et al. Int. J. Dev. Biol. 2014, 58, 379-384
(Non-Patent Document 4) Cristian A. Lasagna-Reeves et al, Neuron, 2016, 92, 407-418
(Non-Patent Document 5) Xinyan Wu et al. Oncotarget, 2017, 8(2), 2971-2983
(Non-Patent Document 6) Daniella M. Schwartz1 et al. Nature Reviews Drug Discovery, 2017, 16, 843-862

The above information disclosed in this Background section is provided only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with the prior art.

As a result of searching for compounds capable of inhibiting the activity of kinases, the present inventors synthesized pyrimidine derivative compounds having various new substituents and identified various kinase inhibitory activities of these novel compounds, thus completing the present invention. These compounds exhibited particularly excellent inhibitory activity on ARK5/NUAK1, ACK1, FLT3, JAK1, JAK2, JAK2 (V617F), JAk3 and the like.

Therefore, it is one aspect of the present invention to provide a novel pyrimidine derivative compound having various substituents.

It is another aspect of the present invention to provide a method for preparing a novel pyrimidine derivative compound having various substituents.

It is another aspect of the present invention to provide a composition containing a novel pyrimidine derivative compound having a variety of substituents as an active ingredient for treating, preventing or palliating leukemia, ovarian cancer, breast cancer, non-small cell carcinoma, colorectal cancer, glioma, and brain protein abnormalities such as Alzheimer's disease, progressive supranuclear palsy and frontotemporal dementia, that is, degenerative diseases caused by Tau deposition.

The objects of the present invention are not limited to those described above. The objects of the present invention will be clearly understood from the following description and could be implemented by means defined in the claims and a combination thereof.

In one aspect, the present invention provides a novel pyrimidine derivative compound represented by the following Formula 1, a stereoisomer thereof, a solvate thereof, or a pharmaceutically acceptable salt thereof:

[Formula 1]

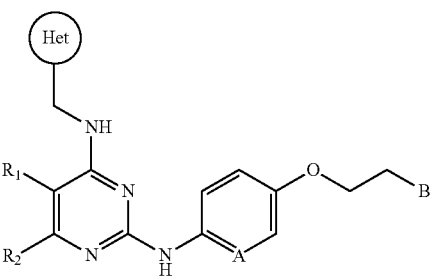

wherein $R_1$ and $R_2$ are each independently a hydrogen atom, a halogen atom, a $C_1$-$C_6$ alkyl group, a $C_1$-$C_6$ haloalkyl group, —O—($C_1$-$C_6$ alkyl), —O—($C_1$-$C_6$ haloalkyl), —C(O)—($C_1$-$C_6$ alkyl), —C(O)—O—($C_1$-$C_6$ alkyl) or —O—C(O)—($C_1$-$C_6$ alkyl), or $R_1$ and $R_2$ are bonded together to form a 5-membered to 6-membered saturated or unsaturated ring, or $R_1$ and $R_2$ are bonded together to form a 5-membered to 6-membered saturated or unsaturated heteroring including one to four heteroatoms selected from nitrogen (N) and oxygen (O) atoms;

Het is a $C_6$-$C_{15}$ aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms;

A is a carbon (C) or nitrogen (N) atom; and

B is a $C_6$-$C_{15}$ aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms.

In one embodiment, $R_1$ and $R_2$ may be each independently a hydrogen atom, methyl, ethyl, $CF_3$, F, Cl or Br, or $R_1$ and $R_2$ may be bonded together to form a 5-membered to 6-membered saturated or unsaturated ring, or $R_1$ and $R_2$ may be bonded together to form a 5-membered to 6-membered saturated or unsaturated heteroring including one to four heteroatoms selected from nitrogen (N) and oxygen (O) atoms;

Het may represent a tetrahydrofuranyl group, a furanyl group, a pyranyl group, a pyridinyl group or a phenyl group; and B may represent a pyrrolidinyl group, a piperidinyl group, a morpholinyl group, a piperazinyl group or an amino group.

In one embodiment, the compound may be selected from the following compounds:

(Compound No. 1) 4-(furan-2-yl)methylamino-5-methyl-2-[4-{2-(pyrrolidin-1-yl) ethoxy}phenylamino]pyrimidine;
(Compound No. 2) 4-(furan-2-yl)methylamino-5-methyl-2-[4-{2-(piperidin-1-yl) ethoxy}phenylamino]pyrimidine;
(Compound No. 3) 4-(furan-2-yl)methylamino-5-methyl-2-[4-{2-(dimethylamino)ethoxy}phenylamino]pyrimidine;
(Compound No. 4) 4-(furan-2-yl)methylamino-5-methyl-2-[2-amino-5-{2-(pyrrolidin-1-yl)ethoxy}pyridine]pyrimidine;
(Compound No. 5) 5-chloro-4-(furan-2-yl)methylamino-2-[4-{2-(pyrrolidin-1-yl) ethoxy}phenylamino]pyrimidine;
(Compound No. 6) 5-chloro-4-(furan-2-yl)methylamino-2-[4-{2-(piperidin-1-yl) ethoxy}phenylamino]pyrimidine;
(Compound No. 7) 5-chloro-4-(furan-2-yl)methylamino-2-[4-{2-(dimethylamino)ethoxy}phenylamino]pyrimidine;
(Compound No. 8) 4-(tetrahydrofuran-2-yl)methylamino-5-methyl-2-[4-{2-(pyrrolidin-1-yl)ethoxy}phenylamino]pyrimidine;
(Compound No. 9) 4-(tetrahydrofuran-2-yl)methylamino-5-methyl-2-[4-{2-(piperidin-1-yl)ethoxy}phenylamino]pyrimidine;
(Compound No. 10) 4-(tetrahydrofuran-2-yl)methylamino-5-methyl-2-[4-{2-(dimethylamino)ethoxy}phenylamino]pyrimidine;
(Compound No. 11) 5-chloro-4-(tetrahydrofuran-2-yl)methylamino-2-[4-{2-(pyrrolidin-1-yl)ethoxy}phenylamino]pyrimidine;
(Compound No. 12) 5-chloro-4-(tetrahydrofuran-2-yl)methylamino-2-[4-{2-(piperidin-1-yl)ethoxy}phenylamino]pyrimidine;
(Compound No. 13) 5-chloro-4-(tetrahydrofuran-2-yl)methylamino-2-[4-{2-(dimethylamino)ethoxy}phenylamino]pyrimidine;
(Compound No. 14) 4-benzylmethylamino-5-methyl-2-[4-{2-(pyrrolidin-1-yl) ethoxy}phenylamino]pyrimidine;
(Compound No. 15) 4-benzylmethylamino-5-methyl-2-[4-{2-(piperidin-1-yl) ethoxy}phenylamino]pyrimidine;
(Compound No. 16) 4-benzylmethylamino-5-methyl-2-[4-{2-(dimethylamino) ethoxy}phenylamino]pyrimidine;
(Compound No. 17) 5-chloro-4-benzylmethylamino-2-[4-{2-(pyrrolidin-1-yl) ethoxy}phenylamino]pyrimidine;
(Compound No. 18) 5-chloro-4-benzylmethylamino-2-[4-{2-(piperidin-1-yl) ethoxy}phenylamino]pyrimidine;
(Compound No. 19) 5-chloro-4-benzylmethylamino-2-[4-{2-(dimethylamino) ethoxy}phenylamino]pyrimidine;
(Compound No. 20) 4-(furan-2-yl) methylamino-5-fluoro-2-[4-{2-(pyrrolidin-1-yl)ethoxy}phenylamino]pyrimidine;
(Compound No. 21) 4-(furan-2-yl) methylamino-5-trifluoromethyl-2-[4-{2-(pyrrolidin-1-yl)ethoxy}phenylamino]pyrimidine;
(Compound No. 22) 4-(furan-2-yl)methylamino-2-[4-{2-(pyrrolidin-1-yl) ethoxy}phenylamino]quinazoline;
(Compound No. 23) 4-(furan-2-yl)methylamino-2-[4-{2-(pyrrolidin-1-yl) ethoxy}phenylamino]-5,6,7,8-tetrahydroquinazoline;
(Compound No. 24) 4-(furan-2-yl)methylamino-2-[4-{2-(pyrrolidin-1-yl) ethoxy}phenylamino]-6,7-dihydro-5H-cyclopenta[d]pyrimidine;
(Compound No. 25) 4-((S)-tetrahydrofuran-2-yl) methylamino-5-methyl-2-[4-{2-(pyrrolidin-1-yl]ethoxy}phenylamino]pyrimidine; and
(Compound No. 26) 5-chloro-4-((S)-tetrahydrofuran-2-yl) methylamino-2-[4-{2-(pyrrolidin-1-yl]ethoxy}phenylamino]pyrimidine.

In another aspect, the present invention provides a pharmaceutical composition for treating, preventing or palliating cancer containing, as an active ingredient, the compound according to the present invention.

In another aspect, the present invention provides a pharmaceutical composition for treating, preventing or palliating a degenerative brain disease containing, as an active ingredient, the compound according to the present invention.

In another aspect, the present invention provides a pharmaceutical composition for treating, preventing or palliating an immunological disease containing g, as an active ingredient, the compound according to the present invention.

In another aspect, the present invention provides a pharmaceutical composition for treating, preventing or palliating an inflammatory disease containing, as an active ingredient, the compound according to the present invention.

In one embodiment, the cancer may include one or more of ovarian cancer, non-small cell carcinoma, colorectal cancer, glioma, breast cancer, esophageal cancer, lung cancer, uterine cancer, pancreatic cancer, prostate cancer and blood cancer.

In one embodiment, the degenerative brain disease may include one or more of Alzheimer's disease, Parkinson's disease, Lewy body dementia and frontotemporal dementia.

Other aspects and preferred embodiments of the invention are discussed infra.

DETAILED DESCRIPTION

Unless context clearly indicates otherwise, all numbers, figures and/or expressions that represent ingredients, reaction conditions and contents of the ingredients used in the specification are approximations that reflect various uncertainties of measurement occurring inherently in obtaining these figures among other things. For this reason, it should be understood that, in all cases, the term "about" modifies all the numbers, figures and/or expressions. In addition, when numerical ranges are disclosed in the description, these numerical ranges are continuous and include all numbers from the minimum to the maximum including the maximum within the ranges unless otherwise defined. Furthermore, when the range is referred to as an integer, it includes all integers from the minimum to the maximum including the maximum within the range, unless otherwise defined.

It should be understood that, in the specification, when the range is referred to regarding a parameter, the parameter encompasses all figures including end points disclosed within the range. For example, the range of "5 to 10" includes figures of 5, 6, 7, 8, 9, and 10, as well as arbitrary sub-ranges such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include figures such as 10%, 11%, 12% and 13%, as well as 30%, and any sub-ranges of 10% to 15%, 12% to 18%, or 20% to 30%, as well as any figures, such as 10.5%, 15.5% and 25.5%, between appropriate integers that fall within the range.

Hereinafter, the present invention will be described in detail.

The compound synthesized in the present invention exhibits kinase inhibitory activity and exhibits a potent effect particularly on ARK5/NUAK1, ACK1, FLT3, JAK1, JAK2, JAK2(V617F) and the like.

The present invention relates to anticancer agents for targeted therapy and compounds having therapeutic effects for dementia and various medical effects, and these substances show such effects through kinase inhibitory activity.

ARK5/NUAK1 kinase, which has the effect of the compound of the present invention, belongs to the adenosine monophosphate-activated protein kinase (AMPK) family and is involved in cell adhesion, migration and metabolism, and stabilization of Tau. ARK5/NUAK1 kinase is involved in the onset of ovarian cancer (Hai-Yan Zhang et al. Oncology Report, 2015, 34, 1193-1202), non-small cell carcinoma (Peng Chen et al. Experimental Lung Research, 2013, 39, 9-17), colorectal cancer, glioma, breast cancer and the like (Abdelhamid Bekri et al. Int. J. Dev. Biol. 2014, 58, 379-384). In addition, the inhibitory activity of this kinase has been reported to be effective in the treatment of brain protein abnormalities such as Alzheimer's disease, progressive supranuclear palsy and frontotemporal dementia, that is, degenerative diseases caused by Tau deposition. Decrease in NUAK1 in rats was identified by reduction in the amount of Tau in the brain and is expected to cause the improvement in cognition (Cristian A. Lasagna-Reeves et al, Neuron, 2016, 92, 407-418).

ACK1 kinase, another kinase that has an effect on the compounds of the present invention, has been shown to be effective on breast cancer, particularly, triple negative breast cancer (TNBC), which is difficult to treat, and is also expressed in esophageal cancer, lung cancer, uterine cancer, pancreatic cancer, prostate cancer and the like (Xinyan Wu et al., Oncotarget, 2017, 8 (2), 2971-2983).

FLT3 kinase, another kinase that has an effect on the compound of the present invention, is highly expressed in acute leukemia (AML), and JAK kinase is associated with cancer such as bone marrow fibrosis and immunological diseases and inflammatory diseases (Daniella M. Schwartz1 et al., Nature Reviews Drug Discovery, 2017, 16, 843-862).

Meanwhile, there are compounds having a structure similar to the compound according to the present invention. For example, PCT International Patent Publication WO 2005/026130 A1 filed by Novarti AG discloses that a compound represented by the following Formula A has kinase inhibitory activity, and PCT International Patent Publication WO 2009/046416 A1 filed by Targegen Inc. discloses that compounds having Formulae B and C each have kinase inhibitory activities, but structurally differ from the present invention.

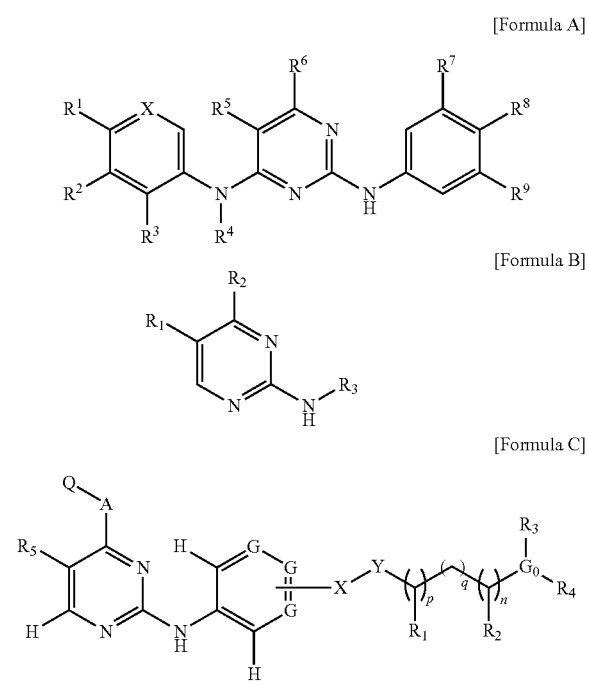

The present invention provides a pyrimidine derivative compound having various substituents represented by the following Formula 1, a solvate thereof, or a pharmaceutically acceptable salt thereof:

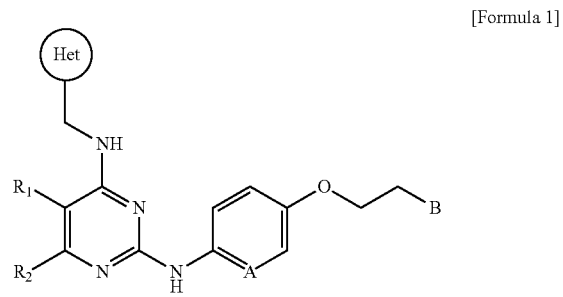

wherein $R_1$ and $R_2$ are each independently a hydrogen atom, a halogen atom, a $C_1$-$C_6$ alkyl group, a $C_1$-$C_6$ haloalkyl group, —O—($C_1$-$C_6$ alkyl), —O—($C_1$-$C_6$ haloalkyl), —C(O)—($C_1$-$C_6$ alkyl), —C(O)—O—($C_1$-$C_6$ alkyl) or —O—C(O)—($C_1$-$C_6$ alkyl), or $R_1$ and $R_2$ are bonded together to form a 5-membered to 6-membered saturated or unsaturated ring, or $R_1$ and $R_2$ are bonded together to form a 5-membered to 6-membered saturated or unsaturated heteroring including one to four heteroatoms selected from nitrogen (N) and oxygen (O) atoms;

Het is a $C_6$-$C_{15}$ aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms;

A is a carbon (C) or nitrogen (N) atom; and

B is a $C_6$-$C_{15}$ aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms.

In one aspect of the invention, $R_1$ and $R_2$ are identical to or different from each other and are each independently $CF_3$, F, Cl or Br, or $R_1$ and $R_2$ are bonded together with a carbon atom or a nitrogen atom, or are bonded together further with at least one heteroatom selected from an oxygen atom and a nitrogen atom, to form a 5-membered or 6-membered saturated or unsaturated heterocyclic group;

Het represents 2-tetrahydrofuranyl, 2(S)-tetrahydrofuranyl, 2(R)-tetrahydrofuranyl, 2-pyranyl, 2-pyridinyl, 3-pyridinyl, 4-pyridinyl, phenyl, 2-trifluoromethylphenyl, 3-trifluoromethylphenyl, 4-trifluoromethylphenyl, 2-halogenphenyl, 3-halogenphenyl, or 4-halogenphenyl;

A represents C or N;

B represents 1-pyrrolidine, dimethylamino, diethylamino, 1-piperidine, 1-morpholine, 4-ethylpiperazine or the like.

Also, the present invention provides a method for preparing the pyrimidine derivative compound having various substituents represented by Formula 1 above, a solvate thereof, or a pharmaceutically acceptable salt thereof.

The pharmaceutically acceptable salt should have low toxicity in humans and should not adversely affect the biological activity and physicochemical properties of the parent compound. The pharmaceutically acceptable salt includes: an acid addition salt of a pharmaceutically applicable free acid and a base compound of Formula 1; an alkali metal salt (such as sodium salt) and an alkaline earth metal salt (such as calcium salt); an organic base addition salt of an organic salt and carboxylic acid of Formula 1; and an amino acid addition salt. The pharmaceutically acceptable salt according to the present invention can be prepared by an ordinary method in the art and includes acid addition salts, for example, salts with inorganic acids such as hydrochloric acid, hydrobromic acid, sulfuric acid, sodium hydrogen sulfate, phosphoric acid, nitric acid and carbonic acid, salts with organic acids such as formic acid, acetic acid, propionic acid, oxalic acid, succinic acid, benzoic acid, citric acid, maleic acid, malonic acid, tartaric acid, gluconic acid, lactic acid, gastric acid, fumaric acid, lactobionic acid, salicylic acid, or acetylsalicylic acid, salts with amino acids such as glycine, alanine, vanillin, isoleucine, serine, cysteine, cystine, asparaginic acid, glutamine, lysine, arginine, tyrosine and proline, and salts with sulfonic acids such as methanesulfonic acid, ethanesulfonic acid, benzenesulfonic acid and toluenesulfonic acid. In addition, the pharmaceutically acceptable salt may be a metal salt prepared by reaction with an alkali metal such as sodium or potassium, or a salt with an ammonium ion. Particularly preferred acid addition salts as the above-mentioned pharmaceutically acceptable salt are hydrochloride and sulfate.

The compound according to the present invention also includes a hydrate or a solvate of the compound represented by Formula 1. The hydrate or solvate may be prepared by an ordinary method. For example, the base compound of Formula 1 may be dissolved in a solvent such as water, methanol, ethanol, acetone or 1,4-dioxane, followed by addition of a free acid or base, and then crystallization or recrystallization.

In addition, the compound represented by Formula 1 may have one or more asymmetric centers, and in the case of such a compound, an enantiomer or diastereomer may exist. Thus, the compound of the present invention includes isomers or a mixture thereof. In addition, different isomers may be separated or degraded by ordinary methods, or any predetermined isomer may be obtained by ordinary synthetic methods or by stereospecific or asymmetric synthesis.

In addition, the compound according to the present invention includes radioactive derivatives of the compound represented by Formula 1, and these radioactive compounds are useful in the field of biological research.

The substituents used to define the compound represented by Formula 1 will be described in more detail as follows.

As used herein, the terms "halo" and "halogen atom", which are used interchangeably with each other, refer to chloro, fluoro, bromo, or iodo.

As used herein, the term "alkyl" refers to a linear, branched or cyclic aliphatic saturated hydrocarbon group having 1 to 10 carbon atoms, preferably 1 to 6 carbon atoms, more preferably 1 to 4 carbon atoms. Specific examples of the alkyl group include a methyl group, an ethyl group, a normal propyl group, an isopropyl group, a cyclopropyl group, a cyclopropylmethyl group, a normal butyl group, an isobutyl group, a tert-butyl group, a cyclobutyl group, a normal pentyl group, an isopentyl group, a neopentyl group, a tert-pentyl group, a cyclopentyl group, a normal hexyl group, an isohexyl group, a cyclohexyl group, a normal heptyl group, a normal octyl group and the like.

As used herein, the term "haloalkyl group" refers to all linear and branched carbon chains having 1 to 13 halogen atoms such as fluoro, chloro, bromo and iodo and having 1 to 10 carbon atoms. Specifically, examples of the haloalkyl group include a fluoromethyl group, a trifluoromethyl group, a 1,2-dichloroethyl group, a 1,1-dichloroethyl group, a pentafluoroethyl group and the like.

As used herein, the term "alkoxy group" means —O—($C_1$-$C_{10}$ alkyl), and specifically, examples thereof includes a methoxy group, an ethoxy group, a propoxy group, a tert-butoxy group, a cyclohexyloxy group and the like.

As used herein, the term "heterocyclic group" refers to a 5-membered or 6-membered aliphatic ring group containing 1 to 2 hetero-atoms selected from nitrogen (N) and oxygen (O) atoms. Specifically, examples of the heterocyclic group include a tetrahydrofuranyl group, a 2,3-dihydrofuranyl group, a 2,5-dihydrofuranyl group, a pyrrolidinyl group, a 2,3-dihydropyrrolidinyl group, a 2,5-dihydropyrrolidinyl group, a tetrahydro-2H-pyranyl group, a 3,4-dihydro-2H-pyranyl group, a 4H-pyranyl group, a piperidinyl group, a 1,2,3,4-tetrahydropyridinyl group, a 1,4-dihydropyridinyl group, a piperazinyl group, an N-protected piperazinyl, a morpholino group and the like. In addition, the heterocyclic group may be substituted or unsubstituted by —OH, a $C_1$-$C_{10}$ alkyl group, —($C_1$-$C_{10}$ hydroxyalkyl), —O—($C_1$-$C_{10}$ alkyl), —C(O)—($C_1$-$C_{10}$ alkyl), or —C(O)NH$_2$.

As used herein, the term "aryl" refers to a monocyclic, bicyclic or tricyclic aromatic hydrocarbon group having 6 to 15 carbon atoms. Specific examples of such an aryl group include a phenyl group, a naphthyl group and the like.

As used herein, the term "heteroaryl" refers to a 5- to 14-membered monocyclic, bicyclic or tricyclic aromatic group containing 1 to 4 hetero-atoms selected from nitrogen (N), oxygen (O) and sulfur (S) atoms. The heteroaryl group may include a thiophenyl group, a pyrrolyl group, a pyrazolyl group, an imidazolyl group, a thiazolyl group, an isothiazolyl group, a pyridinyl group, a pyrazinyl group, a pyridazinyl group, a pyrimidinyl group, an indolyl group, an isoindolyl group, an indazolyl group, a benzimidazolyl group, a benzothiazolyl group, a benzisothiazolyl group, a quinolinyl group, an isoquinolinyl group, a phthalazinyl group, a quinazolinyl group and the like.

Specifically, examples of the novel pyrimidine derivative compound having various substituents represented by Formula 1 according to the present invention include the following compounds:

(Compound No. 1) 4-(furan-2-yl)methylamino-5-methyl-2-[4-{2-(pyrrolidin-1-yl) ethoxy}phenylamino]pyrimidine;
(Compound No. 2) 4-(furan-2-yl)methylamino-5-methyl-2-[4-{2-(piperidin-1-yl) ethoxy}phenylamino]pyrimidine;
(Compound No. 3) 4-(furan-2-yl)methylamino-5-methyl-2-[4-{2-(dimethylamino)ethoxy}phenylamino]pyrimidine;
(Compound No. 4) 4-(furan-2-yl)methylamino-5-methyl-2-[2-amino-5-{2-(pyrrolidin-1-yl)ethoxy}pyridine]pyrimidine;
(Compound No. 5) 5-chloro-4-(furan-2-yl)methylamino-2-[4-{2-(pyrrolidin-1-yl) ethoxy}phenylamino]pyrimidine;
(Compound No. 6) 5-chloro-4-(furan-2-yl)methylamino-2-[4-{2-(piperidin-1-yl) ethoxy}phenylamino]pyrimidine;
(Compound No. 7) 5-chloro-4-(furan-2-yl)methylamino-2-[4-{2-(dimethylamino)ethoxy}phenylamino]pyrimidine;
(Compound No. 8) 4-(tetrahydrofuran-2-yl)methylamino-5-methyl-2-[4-{2-(pyrrolidin-1-yl)ethoxy}phenylamino]pyrimidine;
(Compound No. 9) 4-(tetrahydrofuran-2-yl)methylamino-5-methyl-2-[4-{2-(piperidin-1-yl)ethoxy}phenylamino]pyrimidine;
(Compound No. 10) 4-(tetrahydrofuran-2-yl)methylamino-5-methyl-2-[4-{2-(dimethylamino)ethoxy}phenylamino]pyrimidine;
(Compound No. 11) 5-chloro-4-(tetrahydrofuran-2-yl)methylamino-2-[4-{2-(pyrrolidin-1-yl)ethoxy}phenylamino]pyrimidine;
(Compound No. 12) 5-chloro-4-(tetrahydrofuran-2-yl)methylamino-2-[4-{2-(piperidin-1-yl)ethoxy}phenylamino]pyrimidine;
(Compound No. 13) 5-chloro-4-(tetrahydrofuran-2-yl)methylamino-2-[4-{2-(dimethylamino)ethoxy}phenylamino]pyrimidine;
(Compound No. 14) 4-benzylmethylamino-5-methyl-2-[4-{2-(pyrrolidin-1-yl) ethoxy}phenylamino]pyrimidine;
(Compound No. 15) 4-benzylmethylamino-5-methyl-2-[4-{2-(piperidin-1-yl) ethoxy}phenylamino]pyrimidine;
(Compound No. 16) 4-benzylmethylamino-5-methyl-2-[4-{2-(dimethylamino) ethoxy}phenylamino]pyrimidine;
(Compound No. 17) 5-chloro-4-benzylmethylamino-2-[4-{2-(pyrrolidin-1-yl) ethoxy}phenylamino]pyrimidine;
(Compound No. 18) 5-chloro-4-benzylmethylamino-2-[4-{2-(piperidin-1-yl) ethoxy}phenylamino]pyrimidine;
(Compound No. 19) 5-chloro-4-benzylmethylamino-2-[4-{2-(dimethylamino) ethoxy}phenylamino]pyrimidine;
(Compound No. 20) 4-(furan-2-yl) methylamino-5-fluoro-2-[4-{2-(pyrrolidin-1-yl)ethoxy}phenylamino]pyrimidine;
(Compound No. 21) 4-(furan-2-yl) methylamino-5-trifluoromethyl-2-[4-{2-(pyrrolidin-1-yl)ethoxy}phenylamino]pyrimidine;
(Compound No. 22) 4-(furan-2-yl)methylamino-2-[4-{2-(pyrrolidin-1-yl) ethoxy}phenylamino]quinazoline;
(Compound No. 23) 4-(furan-2-yl)methylamino-2-[4-{2-(pyrrolidin-1-yl) ethoxy}phenylamino]-5,6,7,8-tetrahydroquinazoline;
(Compound No. 24) 4-(furan-2-yl)methylamino-2-[4-{2-(pyrrolidin-1-yl) ethoxy}phenylamino]-6,7-dihydro-5H-cyclopenta[d]pyrimidine;
(Compound No. 25) 4-((S)-tetrahydrofuran-2-yl) methylamino-5-methyl-2-[4-{2-(pyrrolidin-1-yl] ethoxy}phenylamino]pyrimidine; and
(Compound No. 26) 5-chloro-4-((S)-tetrahydrofuran-2-yl) methylamino-2-[4-{2-(pyrrolidin-1-yl] ethoxy}phenylamino]pyrimidine.

Meanwhile, the present invention also provides a method for preparing a novel pyrimidine derivative having various substituents represented by Formula 1.

A method for preparing the compound represented by Formula 1 as a compound according to the present invention includes:

(Step a1) reacting 4,6-dichloropyrimidine represented by the following Formula 2 with an amine compound represented by the following Formula 3 in the presence of a base to prepare a 6-chloro-substituted aminopyrimidine compound represented by the following Formula 3; and

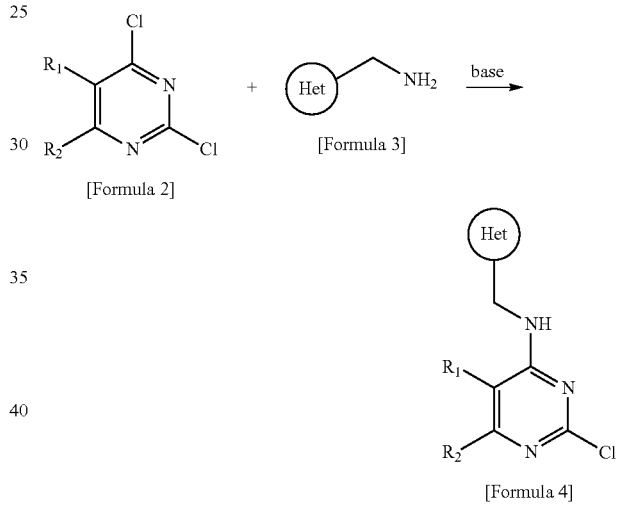

wherein $R_1$, $R_2$ and Het are defined as in Formula 1; and (Step b1) reacting a 6-chloro-4-substituted aminopyrimidine compound represented by the following Formula 4 with an aniline compound represented by the following Formula 5, to prepare a pyrimidine derivative compound having various substituents represented by the following Formula 5:

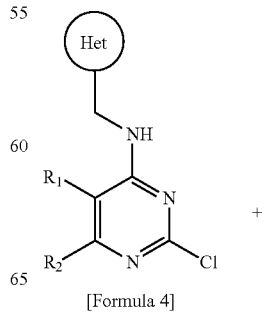

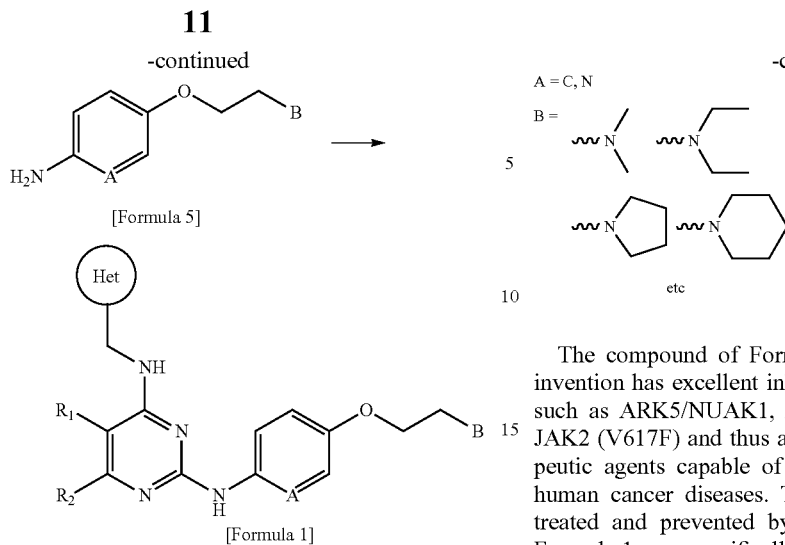

[Formula 5]

[Formula 1]

A = C, N

B = etc wherein Het, $R_1$, $R_2$, A, and B are defined as in Formula 1.

In the preparation method, an amine base is preferably a mono-, di- or tri-alkylamine base, and specifically, examples of the amine base include monomethylamine, dimethylamine, trimethylamine, diisopropylethylamine and the like.

In addition, the reaction solvent used herein may be an ordinary organic solvent. Preferably, the reaction solvent is an alcohol. Specifically, examples of the reaction solvent may include at least one selected from aliphatic alcohols including methanol, ethanol, n-propanol, isopropanol, n-butanol, and the like, and alkoxy alcohols including methoxy methanol, methoxy ethanol, ethoxy ethanol and the like.

In addition, the compounds prepared by the aforementioned preparation method can be purified by an ordinary separation and purification process, for example, by dilution and washing with an organic solvent, and then concentration (suction) of the resulting organic layer under reduced pressure, or by column chromatography, if necessary.

In addition, by introducing various substituent groups into the aniline compound represented by Formula 5 used as a reaction raw material in the preparation method of the present invention, the phenylaminopyridine compound represented by Formula 1, into which various substitution groups are introduced, can be prepared.

The following Reaction Scheme 3 illustrates a representative preparation method for synthesizing the aniline compound represented by Formula 5 having various substituents groups, but the present invention is not limited thereto.

[Reaction Scheme 3]

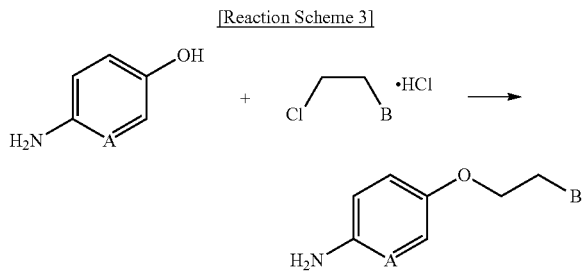

The compound of Formula 1 according to the present invention has excellent inhibitory activities against kinases such as ARK5/NUAK1, ACK1, FLT3, JAK1, JAK2 and JAK2 (V617F) and thus are useful as novel targeted therapeutic agents capable of treating and preventing various human cancer diseases. The cancer diseases that can be treated and prevented by the compound represented by Formula 1 may specifically include ovarian cancer, prostate cancer and breast cancer.

Accordingly, the present invention can be used as an anticancer drug containing, as an active ingredient, the pyrimidine derivative compound having various substituents represented by Formula 1, a stereoisomer thereof, a solvate thereof, or a pharmaceutically acceptable salt thereof.

In addition, the pharmaceutical composition of the present invention contains, as an active ingredient, the pyrimidine derivative compound having various substituents represented by Formula 1, a stereoisomer thereof, a solvate thereof or a pharmaceutically acceptable salt thereof, and formulations for oral administration or formulations for parenteral administration, such as tablets, capsules, troches, liquids and suspensions, which are ordinary formulations in the pharmaceutical field, can be prepared, which can be used for the prevention and treatment of various types of tumors by adding pharmaceutically acceptable carriers, reinforcing agents and excipients to the pharmaceutical composition.

Examples of the excipients which can be used in the pharmaceutical composition of the present invention include sweeteners, binders, solubilizers, solubilizing aids, wetting agents, emulsifiers, isotonizing agents, adsorbents, disintegrants, antioxidants, preservatives, lubricants, fillers, flavoring agents and the like. For example, lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor and the like.

The dose of the compound of Formula 1 according to the present invention may vary depending on the patient's age, body weight, gender, dosage form, health condition and disease severity. The dose is generally 0.01 mg to 5,000 mg a day and may be administered once or several times daily at a predetermined time interval according to the determination of a physician or pharmacist.

Hereinafter, the present invention will be described in more detail with reference to specific examples, preparation examples and test preparations. These examples should not be construed as limiting the scope of the present invention.

EXAMPLE

The following examples are provided only for better understanding of the method for preparing the compound according to the present invention and should not be construed as limiting the scope of the present invention.

Example 1. Preparation of Compound No. 1

Preparation of 4-(furan-2-yl)methylamino-5-methyl-2-[4-{2-(pyrrolidin-1-yl) ethoxy}phenylamino]pyrimidine

Example 1-1. Preparation of 2-chloro-4-(furan-2-yl)methylamino-5-methylpyrimidine

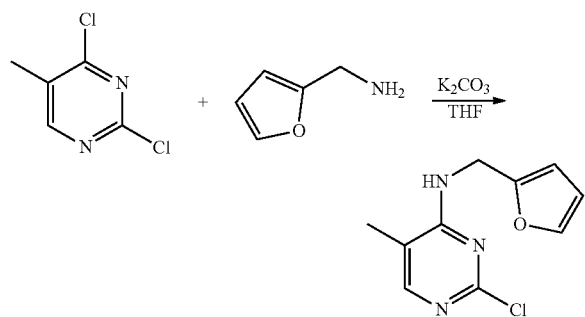

2,4-dichloro-5-methylpyrimidine (1 g, 6.13 mmol) was added to a round bottom flask and dissolved in tetrahydrofuran (40 mL), and then furfurylamine (0.57 mL, 6.13 mmol) and potassium carbonate (2.544 g, 18.4 mmol) were added thereto, followed by stirring at 60° C. for 24 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.99 g, 72%).

NMR analysis of the product identified that the product was 2-chloro-4-(furan-2-yl)methylamino-5-methylpyrimidine. The NMR results were as follows.

$^1$H NMR (400 MHz, CDCl$_3$) δ 1.78-1.81 (m, 4H), 2.60-2.63 (m, 4H), 2.88 (t, J=6.0 Hz, 2H), 4.09 (t, J=6.04 Hz, 2H), 4.64 (d, J=5.64 Hz, 2H), 5.54 (t, J=5.44 Hz, 1H), 6.23 (d, J=3.0 Hz, 1H), 6.32-6.33 (m, 1H), 6.88 (d, J=8.96 Hz, 1H), 7.29 (s, 1H), 7.38 (d, J=1.04 Hz, 1H), 7.41 (s, 1H), 7.43 (s, 1H), 7.89 (s, 1H); $^{13}$C NMR (400 MHz, CDCl$_3$) δ 12.93, 38.07, 108.16, 110.57, 112.12, 142.42, 150.82, 155.06, 158.61, 161.80.

Examples 1-2. Preparation of 4-(2-(pyrrolidin-1-yl)ethoxy)aniline

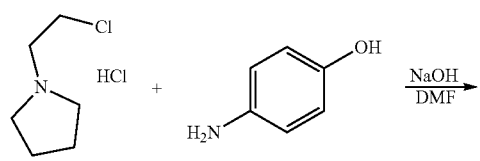

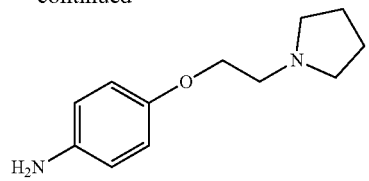

1-(2-chloroethyl)-pyrrolidine hydrochloride (2 g, 11.76 mmol), 4-aminophenol (1.28 g, 11.76 mmol) and sodium hydroxide (1.176 g, 29.4 mmol) were added to a round bottom flask and dissolved in dimethylformamide (15 mL), followed by stirring at 75° C. for 2 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (dichloromethane:methanol, 1:3, v/v) to obtain a compound (0.95 g, 39%).

NMR analysis of the product showed that the product was 4-(2-(pyrrolidin-1-yl)ethoxy)aniline. The NMR results were as follows.

$^1$H NMR (400 MHz, CDCl$_3$) δ 1.65 (s, 4H), 2.46 (s, 4H), 2.66-2.72 (m, 2H), 3.50 (s, 2H), 3.87 (t, J=5.96 Hz, 2H), 6.42 (d, J=8.76 Hz, 2H), 6.60 (d, J=8.72 Hz, 2H); $^{13}$C NMR (400 MHz, CDCl$_3$) δ 23.43, 54.50, 55.12, 67.57, 115.58, 116.06, 140.52, 140.55, 151.57.

Example 1-3. Preparation of 4-(furan-2-yl)methyl-amino-5-methyl-2-[4-{2-(pyrrolidin-1-yl)ethoxy}phenylamino]pyrimidine

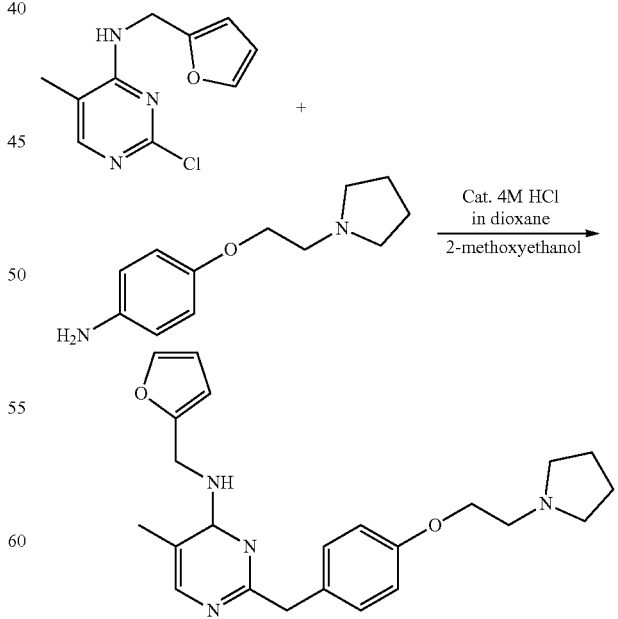

2-chloro-(furan-2-yl)methylamino-5-methylpyrimidine (0.1 g, 0.447 mmol) and 4-(2-(pyrrolidin-1-yl)ethoxy)aniline (0.085 mL, 0.447 mmol) were dissolved in 2-methoxyethanol (9 mL) in a round bottom flask, and hydrochloric acid (0.056 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.140 g, 80%).

NMR analysis of the product identified that the product was 4-(furan-2-yl) methylamino-5-methyl-2-[4-{2-(pyrrolidin-1-yl)ethoxy}phenylamino]pyrimidine. The NMR results were as follows.

mp 171-175° C.; $^1$H NMR (400 MHz, CDCl$_3$) δ 1.80 (s, 4H), 1.94 (s, 3H), 2.61 (s, 4H), 2.88 (t, J=5.96 Hz, 2H), 4.09 (t, J=6 Hz, 2H), 4.67 (d, J=5.32 Hz, 2H), 4.78 (d, J=4.76 Hz, 1H), 6.23 (d, J=2.56 Hz, 1H), 6.33 (s, 1H), 6.87 (d, J=8.92 Hz, 2H), 6.97 (s, 1H), 7.38 (s, 1H), 7.46 (d, J=8.89 Hz, 2H), 7.72 (s, 1H); $^{13}$C NMR (400 MHz, CDCl$_3$) δ 12.94, 23.50, 38.0, 54.71, 55.21, 67.49, 104.24, 107.29, 110.46, 114.86, 120.98, 133.83, 142.07, 152.20, 154.06, 154.65, 159.09, 160.91.

Example 2. Preparation of Compound No. 2

Preparation of 4-(furan-2-yl)methylamino-5-methyl-2-[4-{2-(piperidin-1-yl)ethoxy}phenylamino]pyrimidine Example 2-1. Preparation of 4-(2-(piperidin-1-yl)ethoxy)aniline

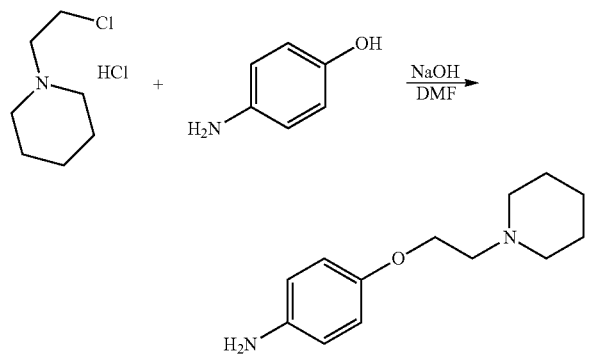

1-(2-chloroethyl)-piperidine hydrochloride (6 g, 32.6 mmol), 4-aminophenol (3.56 g, 32.6 mmol) and sodium hydroxide (3.26 g, 81.5 mmol) were added to a round bottom flask and dissolved in dimethylformamide (40 mL), followed by stirring at 75° C. for 2 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (dichloromethane:methanol, 1:3, v/v) to obtain a compound (4.91 g, 68%); $^1$H NMR (400 MHz, CDCl$_3$) δ 1.39-1.42 (m, 2H), 1.53-1.58 (m, 4H), 2.44 (s, 4H), 2.67 (t, J=6.04 Hz, 2H), 3.57 (s, 2H), 3.96 (t, J=6.08 Hz, 2H), 6.50 (d, J=8.84 Hz, 2H), 6.68 (d, J=8.8 Hz, 2H); $^{13}$C NMR (400 MHz, CDCl$_3$) δ 24.20, 25.89, 54.92, 58.04, 66.45, 115.61, 116.09, 140.49, 151.58.

Example 2-2. Preparation of 4-(furan-2-yl)methylamino-5-methyl-2-[4-{2-(piperidin-1-yl)ethoxy}phenylamino]pyrimidine

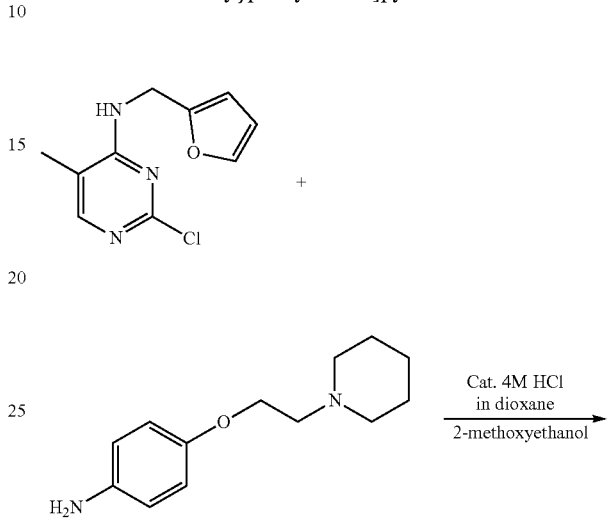

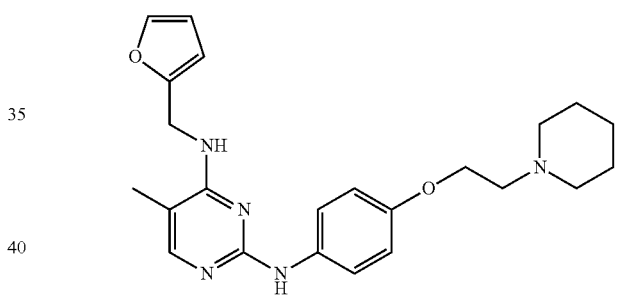

2-chloro-(furan-2-yl)methylamino-5-methylpyrimidine (0.1 g, 0.447 mmol) and 4-(2-(piperidin-1-yl)ethoxy)aniline (98 mg, 0.447 mmol) were dissolved in 2-methoxyethanol (9 mL) in a round bottom flask, hydrochloric acid (0.056 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.19 g, 65%); $^1$H NMR (400 MHz, CDCl$_3$) δ 1.41-1.45 (m, 2H), 1.56-1.62 (m, 4H), 1.91 (s, 3H), 2.49 (s, 4H), 2.74 (t, J=6.12 Hz, 2H), 4.07 (t, J=6.16 Hz, 2H), 4.65 (d, J=5.4 Hz, 2H), 4.87 (t, J=5.48 Hz, 1H), 6.21 (d, J=2.76 Hz, 1H), 6.30-6.31 (m, 1H), 6.85 (d, J=9 Hz, 2H), 7.35-7.36 (m, 1H), 7.44-7.48 (m, 2H), 7.51 (s, 1H), 7.71 (s, 1H); $^{13}$C NMR (400 MHz, CDCl$_3$) δ 12.94, 24.26, 26.00, 37.96, 55.05, 58.07, 66.35, 104.13, 107.26, 110.47, 114.80, 121.02, 134.00, 142.02, 152.28, 153.95, 154.59, 159.17, 160.91.

Example 3. Preparation of Compound No. 3

Preparation of 4-(furan-2-yl)methylamino-5-methyl-2-[4-{2-(dimethylamino)ethoxy}phenylamino]pyrimidine

Example 3-1. Preparation of 4-(2-(dimethylamino)ethoxy)aniline

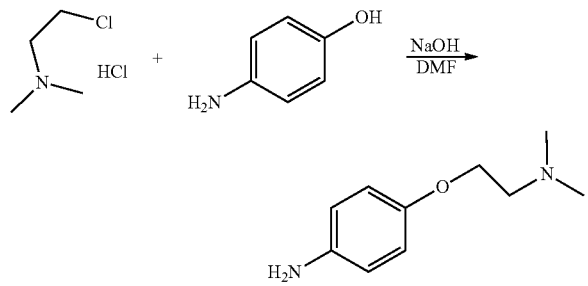

1-(2-chloroethyl)-dimethylamine hydrochloride (6 g, 41.6 mmol), 4-aminophenol (4.54 g, 41.6 mmol) and sodium hydroxide (4.16 g, 104.1 mmol) were added to a round bottom flask and dissolved in dimethylformamide (40 mL), followed by stirring at 75° C. for 2 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (dichloromethane: methanol, 1:3, v/v) to obtain a compound (3.2 g, 46%); $^1$H NMR (400 MHz, CDCl$_3$) δ 2.32 (s, 6H), 2.68 (t, J=5.6 Hz, 2H), 3.50 (s, 2H), 3.98 (t, J=5.6 Hz, 2H), 6.61 (d, J=8.48 Hz, 2H), 6.75 (d, J=8.48 Hz, 2H); $^{13}$C NMR (400 MHz, CDCl$_3$) δ 45.90, 58.45, 66.63, 115.75, 116.32, 140.13, 151.98.

Example 3-2. Preparation of 4-(furan-2-yl)methylamino-5-methyl-2-[4-{2-(dimethylamino)ethoxy}phenylamino]pyrimidine

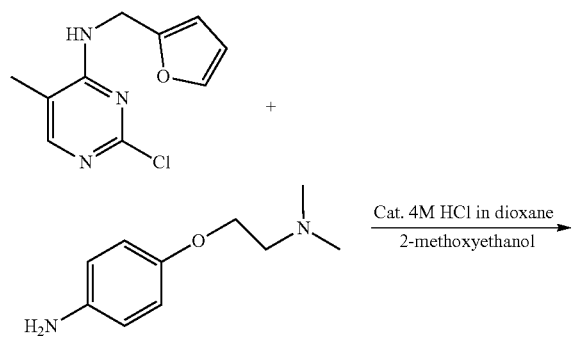

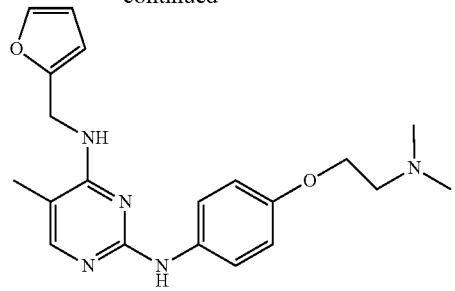

2-chloro-(furan-2-yl)methylamino-5-methylpyrimidine (0.1 g, 0.45 mmol) and 4-(2-(dimethylamino)ethoxy)aniline (0.08 g, 0.447 mmol) were dissolved in 2-methoxyethanol (9 mL) in a round bottom flask, and hydrochloric acid (0.056 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.125 g, 76%); $^1$H NMR (400 MHz, CDCl$_3$) δ 1.89 (s, 3H), 2.31 (s, 6H), 2.69 (t, J=5.76 Hz, 2H), 4.02 (t, J=5.8 Hz, 2H), 4.64 (d, J=5.44 Hz, 2H), 4.94 (t, J=5.44 Hz, 1H), 6.20 (d, J=3.12 Hz, 1H), 6.29-6.30 (m, 1H), 6.86 (d, J=9 Hz, 2H), 7.34 (d, J=1.04 Hz, 1H), 7.47 (d, J=9 Hz, 2H), 7.70 (s, 1H), 7.73 (s, 1H); $^{13}$C NMR (400 MHz, CDCl$_3$) δ 12.94, 37.94, 45.93, 58.41, 66.36, 104.10, 107.24, 110.47, 114.75, 121.01, 134.11, 141.97, 152.31, 153.90, 154.53, 159.19, 160.91.

Example 4. Preparation of Compound No. 4

Preparation of 4-(furan-2-yl)methylamino-5-methyl-2-[2-amino-5-{2-(pyrrolidin-1-yl)ethoxy}pyridine]pyrimidine

Example 4-1. Preparation of 2-amino-5-{2-(pyrrolidin-1-yl)ethoxy}pyridine

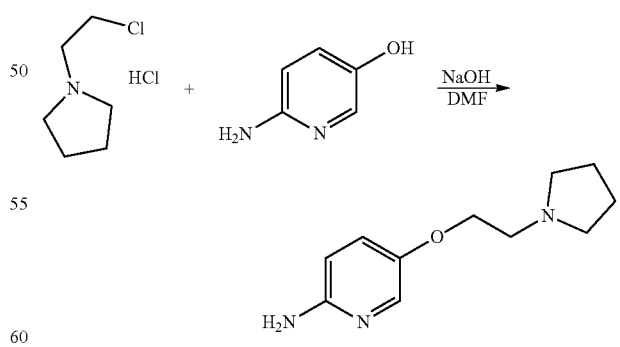

1-(2-chloroethyl)-pyrrolidine hydrochloride (0.464 g, 2.73 mmol), 6-aminopyridin-3-ol (0.4 g, 2.73 mmol) and sodium hydroxide (0.44 g, 10.92 mmol) were added to a round bottom flask and dissolved in dimethylformamide (6 mL), followed by stirring at 75° C. for 2 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (dichloromethane: methanol, 1:3, v/v) to obtain a compound (0.268 g, 47%); $^1$H NMR (400 MHz, CDCl$_3$) δ 1.79-1.82 (m, 4H), 2.48 (s, 1H), 2.59-2.62 (m, 4H), 2.86 (t, J=5.88 Hz, 2H), 4.05 (t, J=5.88 Hz, 2H), 4.23 (s, 2H), 6.47 (d, J=8.88 Hz, 1H), 7.12 (dd, J=2.96 Hz, 8.84 Hz, 1H), 7.79 (d, J=2.84 Hz, 1H); $^{13}$C NMR (400 MHz, CDCl$_3$) δ 23.46, 54.66, 55.17, 68.44, 109.32, 126.57, 134.31, 148.81, 153.05.

Example 4-2. Preparation of 4-(furan-2-yl)methyl-amino-5-methyl-2-[2-amino-5-{2-(pyrrolidin-1-yl) ethoxy}pyridine]pyrimidine

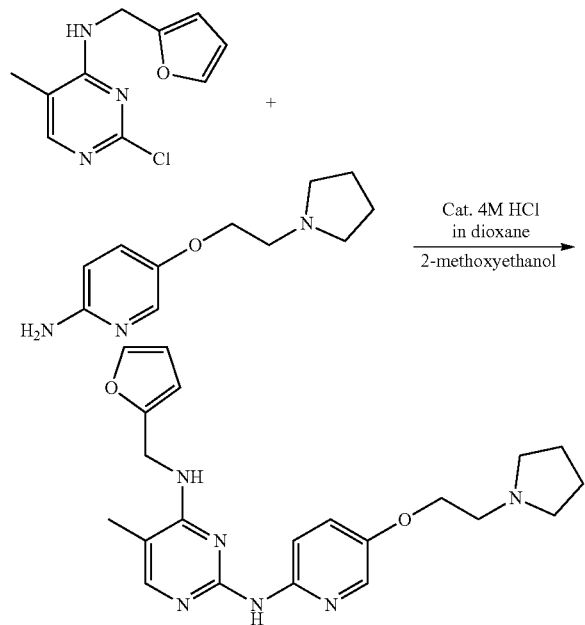

2-chloro-4-(furan-2-yl)methylamino-5-methylpyrimidine (0.1 g, 0.447 mmol) and 2-amino-5-{2-(pyrrolidin-1-yl) ethoxy}pyridine (46 mg, 0.22 mmol), tris (dibenzylideneacetone) dipalladium (0) (41 mg, 0.045 mmol), xantphos (78 mg, 0.13 mmol), and tripotassium phosphate (0.19 g, 0.89 mmol) were dissolved in 1,4-dioxane (6 mL) in a round bottom flask, followed by stirring at 160° C. for 6 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.03 g, 34%); mp 171-175° C.; $^1$H NMR (400 MHz, CDCl$_3$) δ 1.80-1.83 (m, 4H), 1.97 (s, 3H), 2.61-2.64 (m, 4H), 2.89 (t, J=5.88 Hz, 2H), 4.12 (t, J=5.92 Hz, 2H), 4.70 (d, J=5.36 Hz, 2H), 4.81 (t, J=5.04 Hz, 1H), 6.27 (d, J=3.08 Hz, 1H), 6.34-6.35 (m, 1H), 7.24-7.27 (m, 1H), 7.39 (d, J=1.04 Hz, 1H), 7.50 (s, 1H), 7.79 (s, 1H), 7.98 (d, J=2.92 Hz, 1H), 8.25 (d, J=9.12 Hz, 1H); $^{13}$C NMR (400 MHz, CDCl$_3$) δ 12.96, 23.51, 38.10, 54.73, 55.16, 68.17, 105.29, 107.40, 110.50, 112.76, 124.62, 134.83, 142.13, 147.54, 150.31, 152.00, 154.51, 157.72, 160.85.

Example 5. Preparation of Compound No. 5

Preparation of 5-chloro-4-(furan-2-yl)methylamino-2-[4-{2-(pyrrolidin-1-yl) ethoxy}phenylamino]pyrimidine Example 5-1. Preparation of 2,5-dichloro-4-(furan-2-yl) methylaminopyrimidine

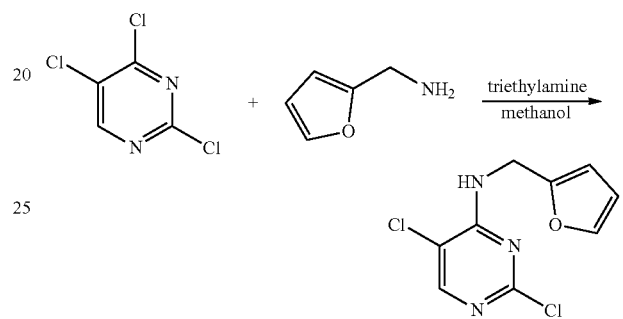

2,4,5-trichloropyrimidine (1.0 g, 5.45 mmol) was added to a round bottom flask and dissolved in methanol (40 mL), and furfurylamine (0.50 mL, 5.45 mmol) and triethylamine (2.28 mL, 16.36 mmol) were added thereto, followed by stirring at 0° C. for 2 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.82 g, 61%); $^1$H NMR (400 MHz, CDCl$_3$) δ 4.71 (d, J=5.52 Hz, 2H), 5.84 (s, 1H), 6.34-6.36 (m, 2H), 7.39 (s, 1H), 8.05 (s, 1H); $^{13}$C NMR (400 MHz, CDCl$_3$) 38.08, 108.46, 110.59, 113.32, 142.66, 150.00, 153.82, 158.41.

Example 5-2. Preparation of 5-chloro-4-(furan-2-yl) methylamino-2-[4-{2-(pyrrolidin-1-yl) ethoxy}phenylamino]pyrimidine

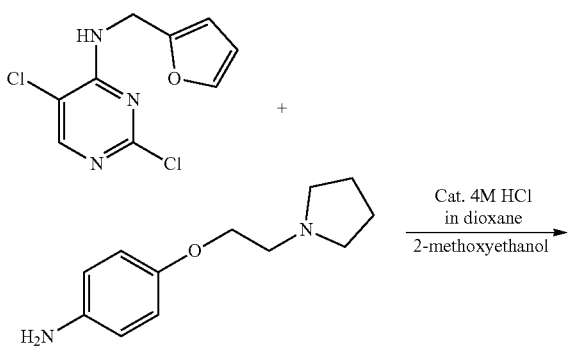

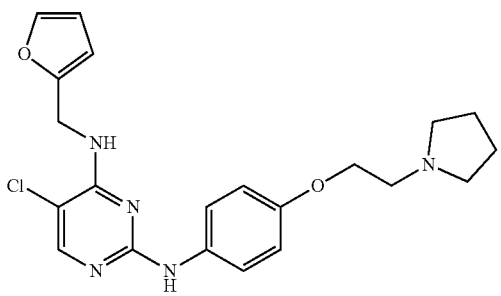

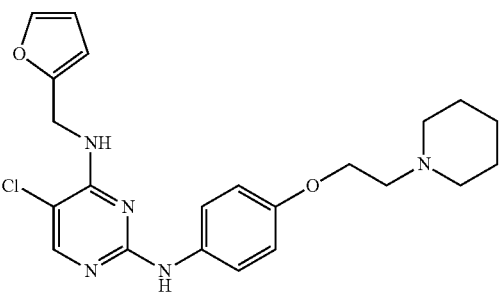

2,5-dichloro-4-(furan-2-yl)methylaminopyrimidine (0.1 g, 0.41 mmol) and 4-(2-(pyrrolidin-1-yl)ethoxy)aniline (78 μL, 0.41 mmol) were dissolved in 2-methoxyethanol (9 mL) in a round bottom flask and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.125 g, 74%); mp 171-175° C.; $^1$H NMR (400 MHz, CDCl$_3$) δ 1.78-1.81 (m, 4H), 2.60-2.63 (m, 4H), 2.88 (t, J=6 Hz, 2H), 4.09 (t, J=6.04 Hz, 2H), 4.64 (d, J=5.6 Hz, 2H), 5.54 (t, J=5.44 Hz, 1H), 6.23 (d, J=3 Hz, 1H), 6.32-6.33 (m, 1H), 6.88 (d, J=8.96 Hz, 2H), 7.29 (s, 1H), 7.38 (s, 1H), 7.42 (d, J=8.96 Hz, 2H), 7.89 (s, 1H); $^{13}$C NMR (400 MHz, CDCl$_3$) δ 23.51, 37.90, 54.72, 55.18, 67.47, 104.30, 107.52, 110.47, 114.85, 121.57, 132.99, 142.27, 151.42, 153.38, 154.63, 157.47, 158.43.

2,5-dichloro-4-(furan-2-yl)methylamino)pyrimidine (0.1 g, 0.41 mmol) and 4-(2-(piperidin-1-yl)ethoxy)aniline (0.09 g, 0.41 mmol) were dissolved in methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 63%); $^1$H NMR (400 MHz, CDCl$_3$) δ 1.35-1.37 (m, 2H), 1.48-1.54 (m, 4H), 2.41 (s, 4H), 2.67 (t, J=6.08 Hz, 2H), 4.00 (t, J=6.12 Hz, 2H), 4.55 (d, J=5.6 Hz, 2H), 5.48 (t, J=5.56 Hz, 1H), 6.13 (dd, J=0.52, 3.16 Hz, 1H), 6.22-6.24 (m, 1H), 6.77 (d, J=9 Hz, 2H), 7.28-7.29 (m, 1H), 7.33 (d, J=8.96 Hz, 2H), 7.53 (s, 1H), 7.80 (s, 1H); $^{13}$C NMR (400 MHz, CDCl$_3$) δ 24.24, 25.98, 37.89, 55.07, 58.04, 66.31, 104.18, 107.52, 110.48, 114.80, 121.62, 133.06, 142.26, 151.44, 153.34, 154.55, 157.46, 158.46.

Example 6. Preparation of Compound No. 6

Preparation of 5-chloro-4-(furan-2-yl)methylamino-2-[4-{2-(piperidin-1-yl)ethoxy}phenylamino]pyrimidine Example 7. Preparation of Compound No. 7

Preparation of 5-chloro-4-(furan-2-yl)methylamino-2-[4-{2-(dimethylamino) ethoxy}phenylamino] pyrimidine

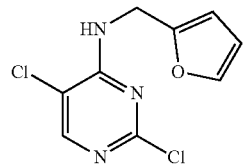

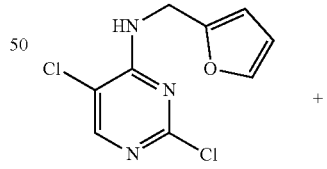

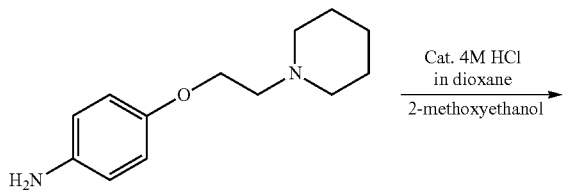

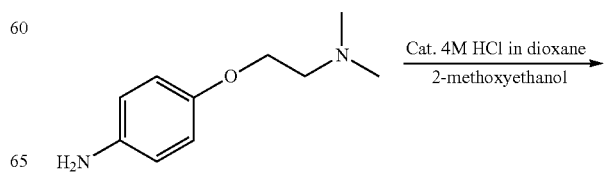

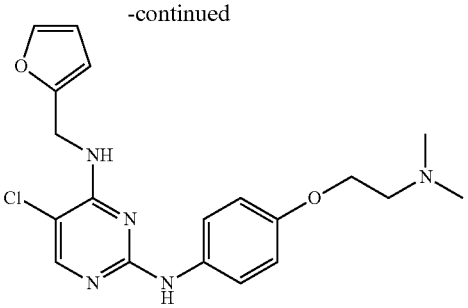

2,5-dichloro-4-(furan-2-yl)methylaminopyrimidine (0.1 g, 0.41 mmol) and 4-(2-(dimethylamino)ethoxy)aniline (73 mg, 0.41 mmol) were dissolved in methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.04 g, 25%); $^1$H NMR (400 MHz, CDCl$_3$) δ 2.33 (s, 6H), 2.72 (t, J=5.76 Hz, 2H), 4.05 (t, J=5.8 Hz, 2H), 4.65 (d, J=5.6 Hz, 2H), 5.54 (t, J=5.48 Hz, 1H), 6.23 (dd, J=0.56, 3.16 Hz, 1H), 6.32-6.34 (m, 1H), 6.88 (d, J=9 Hz, 2H), 7.24 (s, 1H), 7.38 (dd, J=0.72, 1.76 Hz, 1H), 7.42 (d, J=8.96 Hz, 2H), 7.89 (s, 1H); $^{13}$C NMR (400 MHz, CDCl$_3$) δ 37.89, 45.95, 58.40, 66.35, 104.33, 107.53, 110.47, 114.82, 121.55, 133.00, 142.28, 151.41, 153.39, 154.59, 157.46, 158.41.

Example 8. Preparation of Compound No. 8

Preparation of 4-(tetrahydrofuran-2-yl)methyl-amino-5-methyl-2-[4-{2-(pyrrolidin-1-yl)ethoxy}phenylamino]pyrimidine Example 8-1. Preparation of 2-chloro-4-(tetrahydrofuran-2-yl)methylamino-5-methylpyrimidine

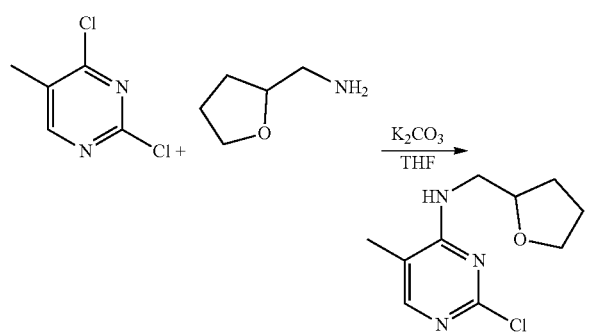

2,4-dichloro-5-methylpyrimidine (1.0 g, 6.13 mmol) was added to a round bottom flask and dissolved in tetrahydrofuran (40 mL), and tetrahydrofurfurylamine (0.63 mL, 6.13 mmol) and potassium carbonate (2.54 g, 18.4 mmol) were added thereto, followed by stirring at 60° C. for 24 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (ethyl acetate:hexane, 1:1, v/v) to obtain a compound (0.87 g, 63%); $^1$H NMR (400 MHz, CDCl$_3$) δ 1.56-1.65 (m, 1H), 1.90-1.97 (m, 2H), 2.01 (s, 3H), 2.03-2.08 (m, 1H), 3.32-3.38 (m, 1H), 3.76-3.92 (m, 3H), 4.06-4.12 (m, 1H), 5.23 (s, 1H), 7.80 (s, 1H); $^{13}$C NMR (400 MHz, CDCl$_3$) δ 12.95, 25.87, 28.77, 44.79, 68.14, 77.40, 112.05, 154.70, 158.59, 162.30.

Example 8-2. Preparation of 4-(tetrahydrofuran-2-yl)methylamino-5-methyl-2-[4-{2-(pyrrolidin-1-yl)ethoxy}phenylamino]pyrimidine

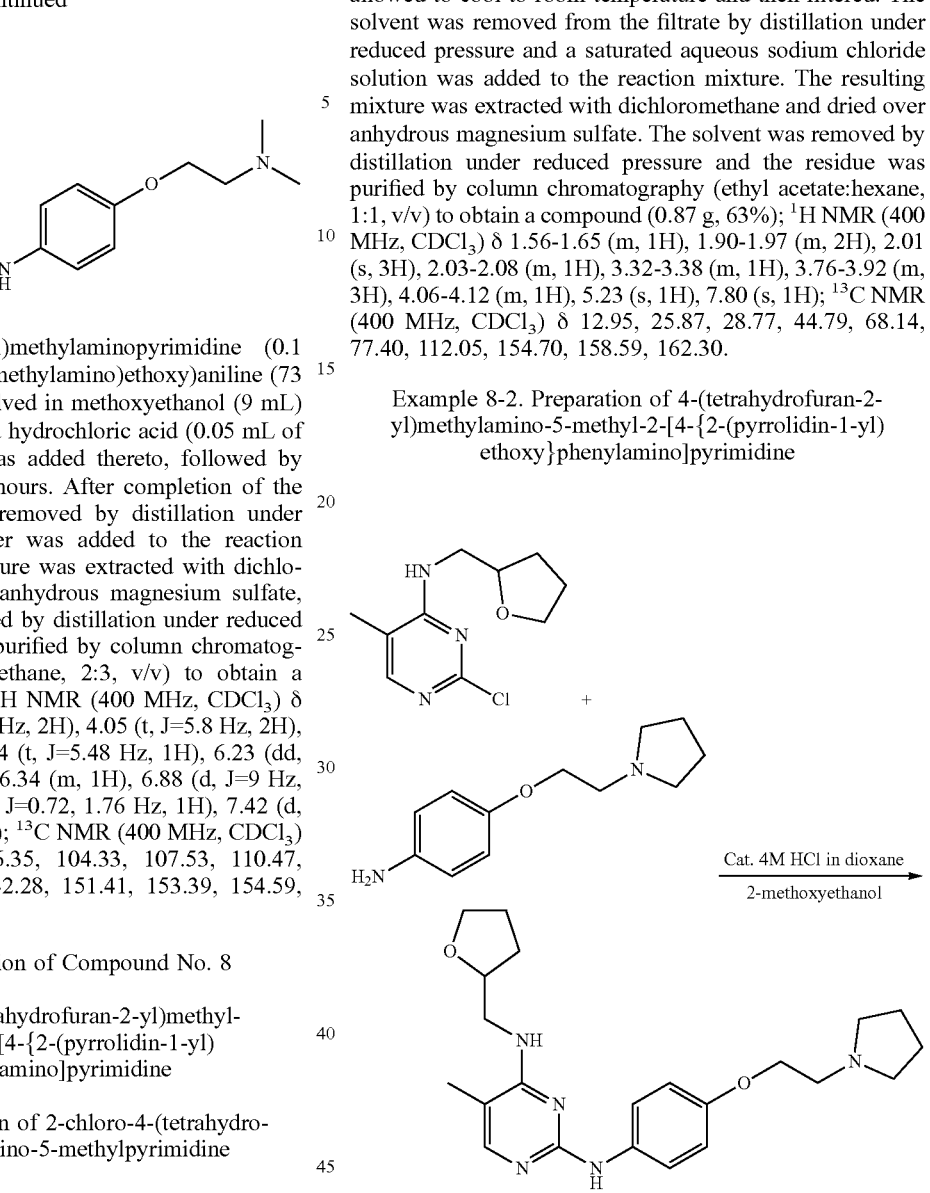

2-chloro-4-(tetrahydrofuran-2-yl)methylamino-5-methylpyrimidine (0.1 g, 0.44 mmol) and 4-(2-(pyrrolidin-1-yl)ethoxy)aniline (0.09 g, 0.44 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (62 mg, 37%); $^1$H NMR (400 MHz, CDCl$_3$) δ 1.56-1.65 (m, 1H), 1.80 (t, J=3.12 Hz, 4H), 1.87-1.93 (m, 5H), 1.96-2.03 (m, 1H), 2.61 (s, 4H), 2.88 (t, J=6.04 Hz, 2H), 3.35-3.41 (m, 1H), 3.75-3.86 (m, 2H), 3.86-3.91 (m, 1H), 4.08 (t, J=6.08 Hz, 2H), 4.13 (s, 1H), 4.95 (t, J=5.32 Hz, 1H), 6.86 (d, J=8.88 Hz, 2H), 7.18 (s, 1H), 7.47 (d, J=8.88 Hz, 1H), 7.69 (s, 1H); $^{13}$C NMR (400 MHz, CDCl$_3$) δ 13.00, 23.50, 25.92, 28.80, 44.67, 54.71, 55.21, 67.49, 68.13, 77.81, 104.25, 114.80, 120.78, 134.10, 153.88, 154.28, 159.13, 161.44.

Example 9. Preparation of Compound No. 9

Preparation of 4-(tetrahydrofuran-2-yl)methyl-amino-5-methyl-2-[4-{2-(piperidin-1-yl)ethoxy}phenylamino]pyrimidine

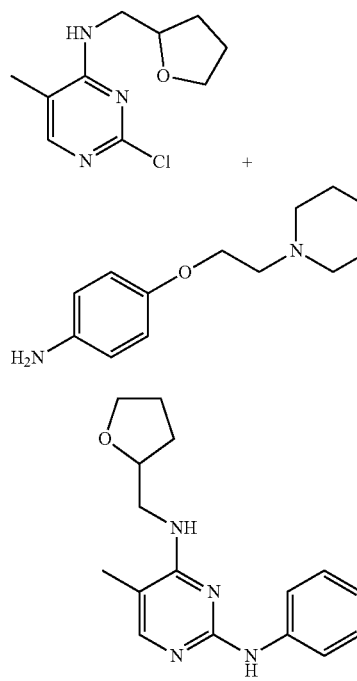

2-chloro-4-(tetrahydrofuran-2-yl)methylamino-5-methyl-pyrimidine (0.1 g, 0.44 mmol) and 4-(2-(piperidin-1-yl)ethoxy)aniline (97 mg, 0.44 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (85 mg, 47%); $^1$H NMR (400 MHz, CDCl$_3$) δ 1.43-1.47 (m, 2H), 1.58-1.65 (m, 5H), 1.89-1.94 (m, 2H), 1.95 (s, 3H), 2.00-2.04 (m, 1H), 2.50 (s, 4H), 2.76 (t, J=6.16 Hz, 2H), 3.36-3.43 (m, 1H), 3.76-3.83 (m, 2H), 3.87-3.92 (m, 1H), 4.07-4.15 (m, 3H), 4.87 (t, J=5.28 Hz, 1H), 6.64 (s, 1H), 6.86 (d, J=8.96 Hz, 2H), 7.46 (d, J=9 Hz, 2H), 7.69 (s, 1H); $^{13}$C NMR (400 MHz, CDCl$_3$) δ 13.01, 24.24, 25.94, 25.99, 28.81, 44.66, 55.06, 58.06, 66.36, 68.15, 77.81, 104.30, 114.81, 120.78, 134.03, 153.86, 154.27, 159.09, 161.44.

Example 10. Preparation of Compound No. 10

Preparation of 4-(tetrahydrofuran-2-yl)methyl-amino-5-methyl-2-[4-{2-(dimethylamino)ethoxy}phenylamino]pyrimidine

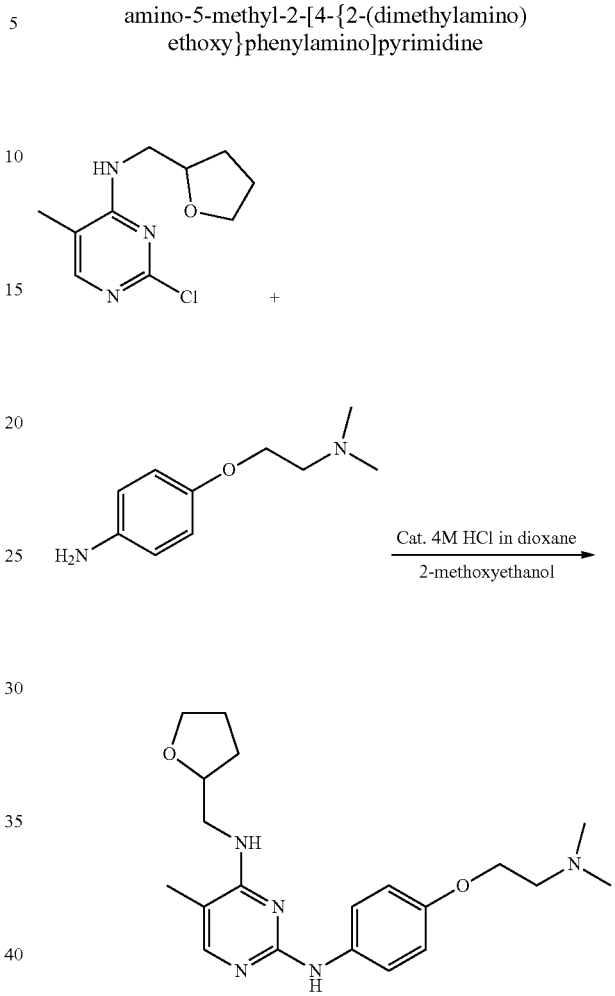

2-chloro-4-(tetrahydrofuran-2-yl)methylamino-5-methyl-pyrimidine (0.1 g, 0.44 mmol) and 4-(2-(dimethylamino)ethoxy)aniline (79 mg, 0.44 mmol) were dissolved in 2-methoxyethanol (9 mL) in a round bottom flask, and hydrochloric acid (55 μL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 70%); $^1$H NMR (400 MHz, CDCl$_3$) δ 1.55-1.64 (m, 1H), 1.86-1.92 (m, 5H), 1.96-2.02 (m, 1H), 2.33 (s, 6H), 2.70 (t, J=5.76 Hz, 2H), 3.34-3.41 (m, 1H), 3.74-3.82 (m, 2H), 3.85-3.91 (m, 1H), 4.04 (t, J=5.76 Hz, 2H), 4.09-4.15 (m, 1H), 5.00 (t, J=5.28 Hz, 1H), 6.86 (d, J=8.88 Hz, 2H), 7.41 (s, 1H), 7.47 (d, J=8.88 Hz, 2H), 7.69 (s, 1H); $^{13}$C NMR (400 MHz, CDCl$_3$) δ 13.00, 25.91, 28.80, 44.69, 45.92, 58.41, 66.38, 68.11, 77.81, 104.20, 114.75, 120.76, 134.20, 153.79, 154.22, 159.14, 161.43.

Example 11. Preparation of Compound No. 11

Preparation of 5-chloro-4-(tetrahydrofuran-2-yl)
methylamino-2-[4-{2-(pyrrolidin-1-yl)
ethoxy}phenylamino]pyrimidine

Example 11-1. Preparation of 2,5-dichloro-4-(tetrahydrofuran-2-yl)methylamino pyrimidine

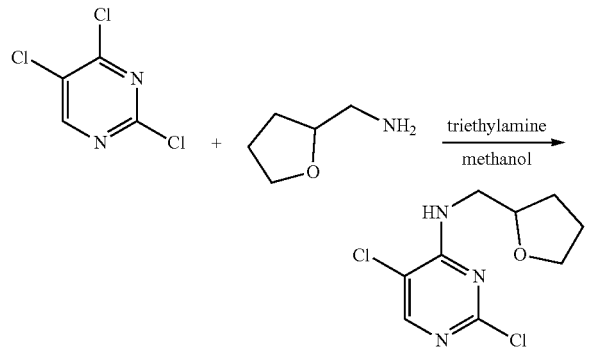

2,4,5-trichloropyrimidine (1.0 g, 5.45 mmol) was added to a round bottom flask and dissolved in methanol (40 mL), and tetrahydrofurfurylamine (0.55 g, 5.45 mmol) and triethylamine (2.28 mL, 16.35 mmol) were added thereto, followed by stirring at 0° C. for 2 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.83 g, 62%); $^1$H NMR (400 MHz, CDCl$_3$) δ 1.56-1.64 (m, 1H), 1.91-1.98 (m, 2H), 2.02-2.10 (m, 1H), 3.38-3.45 (m, 1H), 3.77-3.86 (m, 2H), 3.89-3.94 (m, 1H), 4.07-4.13 (m, 1H), 5.91 (s, 1H), 8.02 (s, 1H); $^{13}$C NMR (400 MHz, CDCl$_3$) δ 25.90, 28.76, 44.84, 68.28, 76.96, 113.31, 153.53, 158.40, 158.88.

Example 11-2. Preparation of 5-chloro-4-(tetrahydrofuran-2-yl)methylamino-2-[4-{2-(pyrrolidin-1-yl)ethoxy}phenylamino]pyrimidine

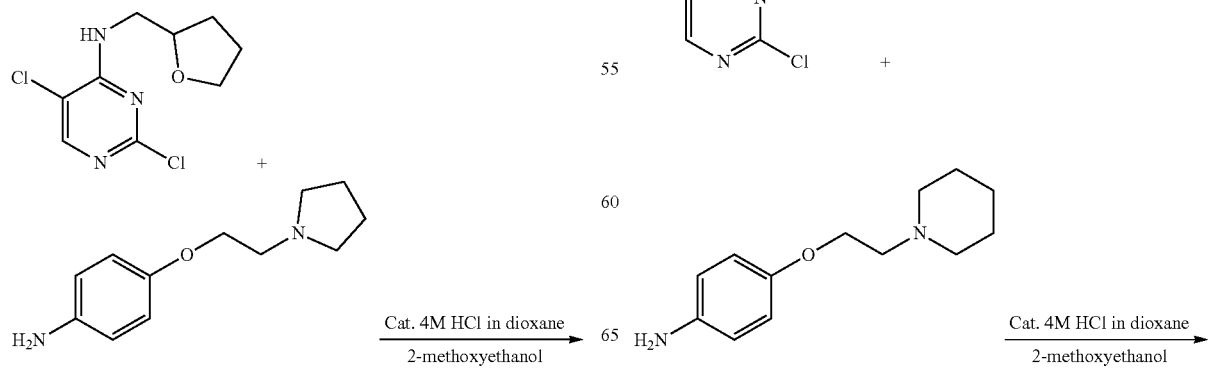

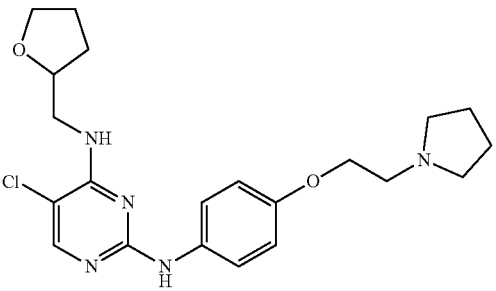

2,5-dichloro-4-(tetrahydrofuran-2-yl)methylaminopyrimidine (0.1 g, 0.4 mmol) and 4-(2-(pyrrolidin-1-yl)ethoxy)aniline (83 mg, 0.4 mmol) were dissolved in 2-methoxyethanol (9 mL) in a round bottom flask and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 63%); $^1$H NMR (400 MHz, CDCl$_3$) δ 1.55-1.63 (m, 1H), 1.80 (s, 4H), 1.87-1.94 (m, 2H), 1.95-2.03 (m, 1H), 2.62 (s, 4H), 2.88 (t, J=5.96 Hz, 2H), 3.39-3.46 (m, 1H), 3.69-6.80 (m, 2H), 3.87-3.92 (m, 1H), 4.09 (t, J=6.04 Hz, 3H), 5.64 (t, J=5.44 Hz, 1H), 6.81 (d, J=8.92 Hz, 2H), 7.42 (d, J=8.88 Hz, 2H), 7.56 (s, 1H), 7.86 (s, 1H); $^{13}$C NMR (400 MHz, CDCl$_3$) δ 23.50, 25.91, 28.77, 44.59, 54.71, 55.17, 67.44, 68.23, 77.46, 104.31, 114.78, 121.39, 133.25, 153.05, 154.44, 157.95, 158.47.

Example 12. Preparation of Compound No. 12

Preparation of 5-chloro-4-(tetrahydrofuran-2-yl)
methylamino-2-[4-{2-(piperidin-1-yl)
ethoxy}phenylamino]pyrimidine

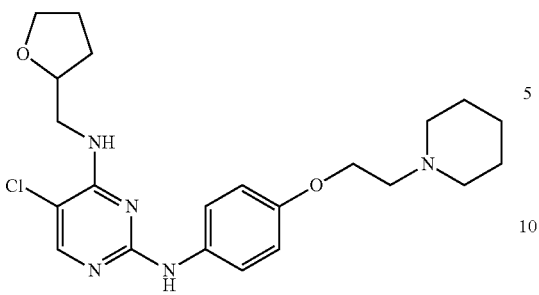

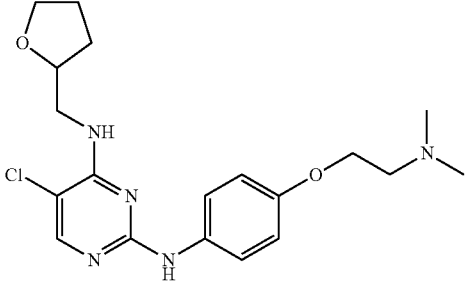

2,5-dichloro-4-(tetrahydrofuran-2-yl)methylaminopyrimidine (0.1 g, 0.4 mmol) and 4-(2-(piperidin-1-yl)ethoxy)aniline (89 mg, 0.4 mmol) were dissolved in 2-methoxyethanol (9 mL) in a round bottom flask and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.13 g, 72%); $^1$H NMR (400 MHz, CDCl$_3$) δ 1.44-1.47 (m, 2H), 1.58-1.64 (m, 5H), 1.89-1.97 (m, 2H), 1.97-2.05 (m, 1H), 2.50 (s, 4H), 2.76 (t, J=6.12 Hz, 2H), 3.41-3.47 (m, 1H), 3.70-3.76 (m, 1H), 3.78-3.82 (m, 1H), 3.89-3.94 (m, 1H), 4.07-4.12 (m, 3H), 5.58 (t, J=5.36 Hz, 1H), 6.75 (s, 1H), 6.87 (d, J=8.96 Hz, 2H), 7.42 (d, J=8.96 Hz, 2H), 7.87 (s, 1H); $^{13}$C NMR (400 MHz, CDCl$_3$) δ 24.23, 25.93, 25.99, 28.78, 44.57, 55.08, 58.04, 66.35, 68.27, 77.46, 104.51, 114.83, 121.36, 133.11, 153.11, 154.47, 157.97, 158.41.

2,5-dichloro-4-(tetrahydrofuran-2-yl)methylaminopyrimidine (0.1 g, 0.4 mmol) and 4-(2-(dimethylamino)ethoxy)aniline (73 mg, 0.4 mmol) were dissolved in 2-methoxyethanol (9 mL) in a round bottom flask and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (95 mg, 60%); $^1$H NMR (400 MHz, CDCl$_3$) δ 1.55-1.63 (m, 1H), 1.87-1.94 (m, 2H), 1.95-2.01 (m, 1H), 2.33 (s, 6H), 2.71 (t, J=5.68 Hz, 2H), 3.39-3.46 (m, 1H), 3.69-3.80 (m, 2H), 3.87-3.92 (m, 1H), 4.04 (t, J=5.68 Hz, 2H), 4.09-4.11 (m, 1H), 5.65 (t, J=5.24 Hz, 1H), 6.87 (d, J=8.8 Hz, 2H), 7.43 (d, J=8.84 Hz, 2H), 7.57 (s, 1H), 7.86 (s, 1H); $^{13}$C NMR (400 MHz, CDCl$_3$) δ 25.91, 28.77, 44.59, 45.93, 58.39, 66.34, 68.23, 77.46, 104.31, 114.75, 121.38, 133.28, 153.05, 154.40, 157.95, 158.46.

Example 14. Preparation of Compound No. 14

Example 14-1. Preparation of 2-chloro-4-benzylmethylamino-5-methylpyrimidine

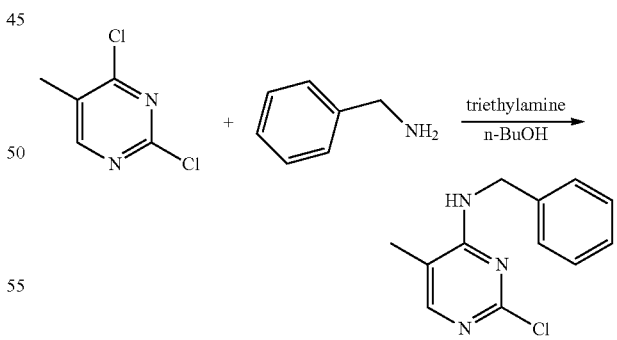

2,4-dichloro-5-methylpyrimidine (1 g, 6.13 mmol) was added to a round bottom flask and dissolved in n-butanol (30 mL), and then benzylamine (0.67 mL, 6.13 mmol) and triethylamine (2.57 mL, 18.4 mmol) were added thereto, followed by stirring at 110° C. for 2 hours. After completion of the reaction, the solvent was removed by distillation under reduced pressure and water was added to the reaction mixture. The resulting mixture was extracted with dichloromethane and dried over anhydrous magnesium sulfate, Example 13. Preparation of Compound No. 13

Preparation of 5-chloro-4-(tetrahydrofuran-2-yl)methylamino-2-[4-{2-(dimethylamino)ethoxy}phenylamino]pyrimidine

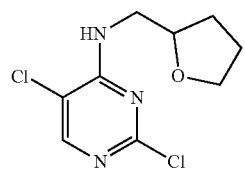

+

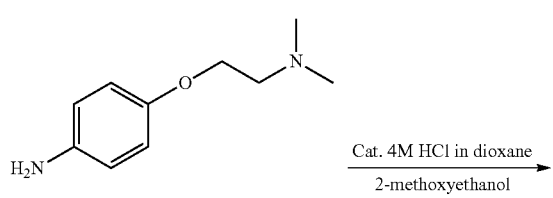

and the solvent was removed by distillation under reduced pressure. The residue was purified by column chromatography (ethyl acetate:hexane, 1:1, v/v) to obtain a compound (1.15 g, 80%); $^1$H NMR (400 MHz, CDCl$_3$) δ 1.99 (s, 3H), 4.70 (d, J=5.4 Hz, 2H), 4.98 (s, 1H), 7.30-7.39 (m, 5H), 7.83 (d, J=0.8 Hz, 1H); $^{13}$C NMR (400 MHz, CDCl$_3$) δ 13.00, 45.29, 111.85, 127.87, 128.11, 128.87, 137.89, 155.01, 158.80, 162.06.

Example 14-2. Preparation of 4-benzylmethyl-amino-5-methyl-2-[4-{2-(pyrrolidin-1-yl)ethoxy}phenylamino]pyrimidine

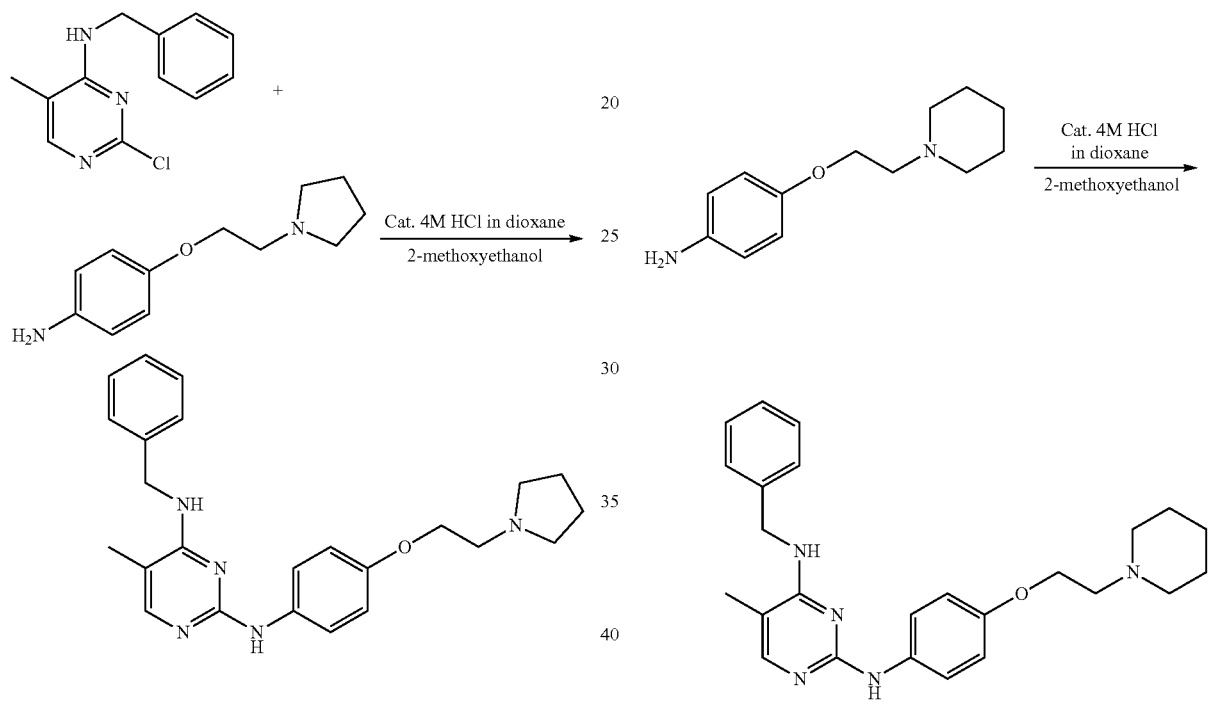

2-chloro-4-benzylmethylamino-5-methylpyrimidine (0.1 g, 0.428 mmol) and 4-(2-(pyrrolidin-1-yl)ethoxy)aniline (88 mg, 0.43 mmol) were dissolved in 2-methoxyethanol (9 mL) in a round bottom flask, and hydrochloric acid (53 μL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.14 g, 82%); $^1$H NMR (400 MHz, CDCl$_3$) δ 1.76-1.79 (m, 4H), 1.90 (s, 3H), 2.57-2.60 (m, 4H), 2.85 (t, J=6 Hz, 2H), 4.04 (t, J=6.04 Hz, 2H), 4.66 (d, J=5.56 Hz, 2H), 4.89 (t, J=5.52 Hz, 1H), 6.79 (d, J=9 Hz, 2H), 7.23-7.27 (m, 1H), 7.29-7.32 (m, 4H), 7.38 (d, J=9 Hz, 2H), 7.60 (s, 1H), 7.71 (s, 1H); $^{13}$C NMR (400 MHz, CDCl$_3$) δ 13.07, 23.54, 44.87, 54.72, 55.23, 67.45, 103.91, 114.79, 120.89, 127.30, 127.57, 128.65, 134.08, 139.26, 153.86, 154.47, 159.30, 161.23.

Example 15. Preparation of Compound No. 15

Preparation of 4-benzylmethylamino-5-methyl-2-[4-{2-(piperidin-1-yl)ethoxy}phenylamino] pyrimidine

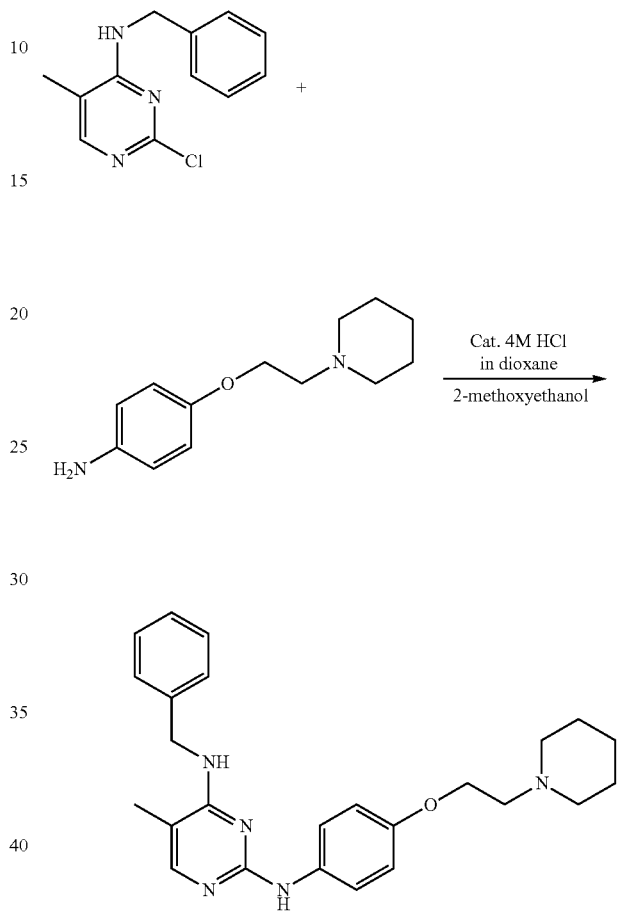

2-chloro-4-benzylmethylamino-5-methylpyrimidine (0.1 g, 0.43 mmol) and 4-(2-(piperidin-1-yl)ethoxy)aniline (94 mg, 0.42 mmol) were dissolved in 2-methoxyethanol (9 mL) in a round bottom flask and hydrochloric acid (53 μL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (99 mg, 55%); $^1$H NMR (400 MHz, CDCl$_3$) δ 1.33-1.36 (m, 2H), 1.47-1.52 (m, 4H), 1.81 (s, 3H), 2.39 (s, 4H), 2.64 (t, J=6.08 Hz, 2H), 3.95 (t, J=6.12 Hz, 2H), 4.57 (d, J=5.6 Hz, 2H), 4.78 (t, J=5.56 Hz, 1H), 6.69 (d, J=9 Hz, 2H), 7.15-7.18 (m, 1H), 7.20-7.25 (m, 4H), 7.29 (d, J=8.96 Hz, 2H), 7.44 (s, 1H), 7.61 (s. 1H); $^{13}$C NMR (400 MHz, CDCl$_3$) δ 13.07, 24.28, 26.01, 44.89, 55.06, 58.08, 66.33, 103.93, 114.80, 120.91, 127.32, 127.58, 128.66, 134.04, 139.24, 153.85, 154.47, 159.28, 161.23.

Example 16. Preparation of Compound No. 16

Preparation of 4-benzylmethylamino-5-methyl-2-[4-{2-(dimethylamino)ethoxy}phenylamino] pyrimidine

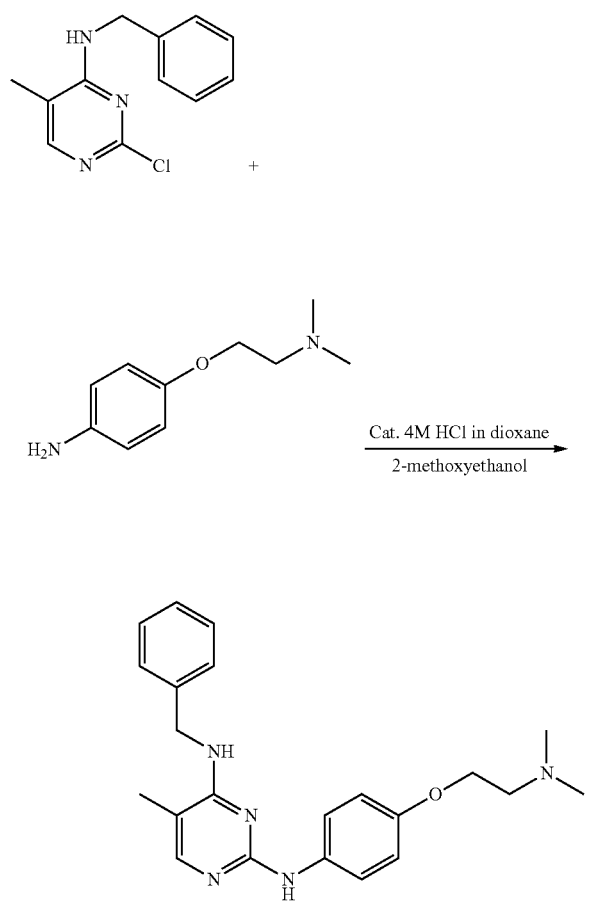

2-chloro-4-benzylmethylamino-5-methylpyrimidine (0.1 g, 0.428 mmol) and 4-(2-(dimethylamino)ethoxy)aniline (77 mg, 0.43 mmol) were dissolved in 2-methoxyethanol (9 mL) in a round bottom flask and hydrochloric acid (53 µL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.09 g, 56%); $^1$H NMR (400 MHz, CDCl$_3$) δ 1.82 (s, 3H), 2.22 (s, 6H), 2.60 (t, J=5.76 Hz, 2H), 3.91 (t, J=5.8 Hz, 2H), 4.57 (d, J=5.56 Hz, 2H), 4.79 (t, J=5.36 Hz, 1H), 6.70 (d, J=9.0 Hz, 2H), 7.15-7.19 (m, 1H), 7.21-7.24 (m, 4H), 7.30 (d, J=9.0 Hz, 2H), 7.39 (s, 1H), 7.62 (s, 1H); $^{13}$C NMR (400 MHz, CDCl$_3$) δ 13.07, 44.88, 45.95, 58.43, 66.37, 103.94, 114.78, 120.87, 127.32, 127.57, 128.66, 134.06, 139.23, 153.85, 154.47, 159.27, 161.23.

Example 17. Preparation of Compound No. 17

Example 17-1. Preparation of 2,5-dichloro-4-benzylmethylaminopyrimidine

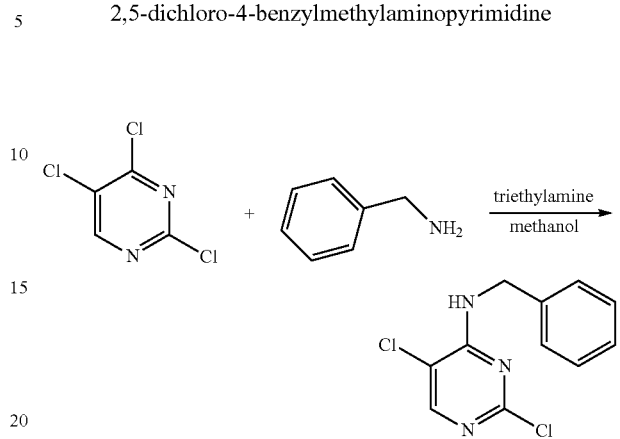

2,4,5-trichloropyrimidine (1.0 g, 5.45 mmol) was added to a round bottom flask and dissolved in methanol (30 mL), and then benzylamine (0.60 mL, 5.45 mmol) and triethylamine (2.28 mL, 16.35 mmol) were added thereto, followed by stirring at 0° C. for 2 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.67 g, 48%); $^1$H NMR (400 MHz, CDCl$_3$) δ 4.71 (d, J=5.6 Hz, 2H), 5.79 (s, 1H), 7.31-7.40 (m, 5H), 8.04 (s, 1H); $^{13}$C NMR (400 MHz, CDCl$_3$) δ 45.28, 113.20, 128.01, 128.05, 128.94, 137.05, 153.72, 158.55, 158.64.

Example 17-2. Preparation of 5-chloro-4-benzylmethylamino-2-[4-{2-(pyrrolidin-1-yl)ethoxy}phenylamino] pyrimidine

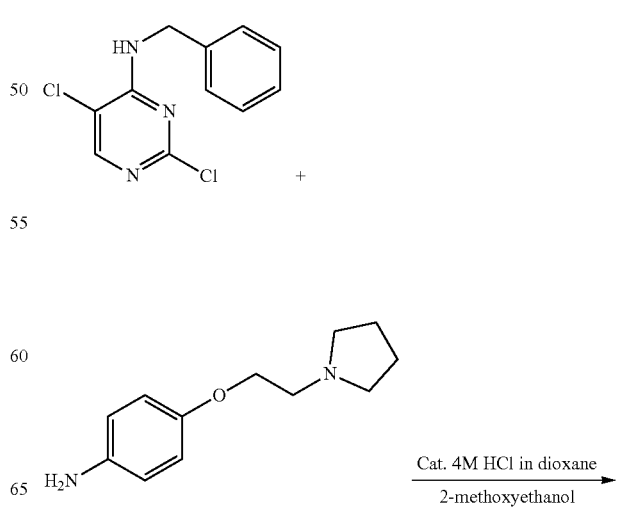

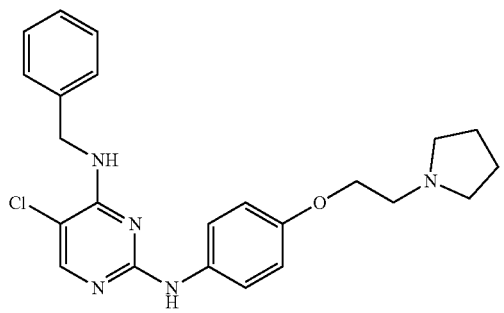

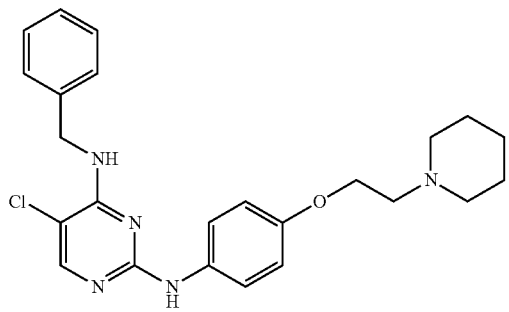

2,5-dichloro-4-benzylmethylaminopyrimidine (0.1 g, 0.39 mmol) and 4-(2-(pyrrolidin-1-yl)ethoxy)aniline (81 mg, 0.39 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.12 g, 68%); $^1$H NMR (400 MHz, CDCl$_3$) δ 1.70 (s, 4H), 2.51 (s, 4H), 2.78 (t, J=6 Hz, 2H), 3.97 (t, J=6 Hz, 2H), 4.55 (d, J=5.68 Hz, 2H), 5.50 (t, J=5.56 Hz, 1H), 6.72 (d, J=8.92 Hz, 2H), 7.15-7.26 (m, 7H), 7.53 (s, 1H), 7.80 (s, 1H); $^{13}$C NMR (400 MHz, CDCl$_3$) δ 23.54, 44.83, 54.74, 55.20, 67.43, 104.08, 114.81, 121.49, 127.49, 127.50, 128.72, 133.11, 138.37, 153.25, 154.50, 157.74, 158.57.

2,5-dichloro-4-benzylmethylaminopyrimidine (0.1 g, 0.39 mmol) and 4-(2-(piperidin-1-yl)ethoxy)aniline (86 mg, 0.39 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.142 g, 83%); $^1$H NMR (400 MHz, CDCl$_3$) δ 1.43-1.46 (m, 2H), 1.58-1.64 (m, 4H), 2.52 (s, 4H), 2.77 (t, J=6 Hz, 2H), 4.07 (t, J=6.04 Hz, 2H), 4.64 (d, J=5.72 Hz, 2H), 5.61 (t, J=5.68 Hz, 1H), 6.79 (d, J=8.96 Hz, 2H), 7.25-7.37 (m, 7H), 7.73 (s, 1H), 7.88 (s, 1H); $^{13}$C NMR (400 MHz, CDCl$_3$) δ 24.14, 25.83, 44.82, 55.00, 57.95, 66.13, 104.05, 114.80, 121.48, 127.48, 127.50, 128.72, 133.18, 138.37, 153.17, 154.35, 157.74, 158.54.

Example 18. Preparation of Compound No. 18

Preparation of 5-chloro-4-benzylmethylamino-2-[4-{2-(piperidin-1-yl)ethoxy}phenylamino] pyrimidine Example 19. Preparation of Compound No. 19

Preparation of 5-chloro-4-benzylmethylamino-2-[4-{2-(dimethylamino)ethoxy}phenylamino] pyrimidine

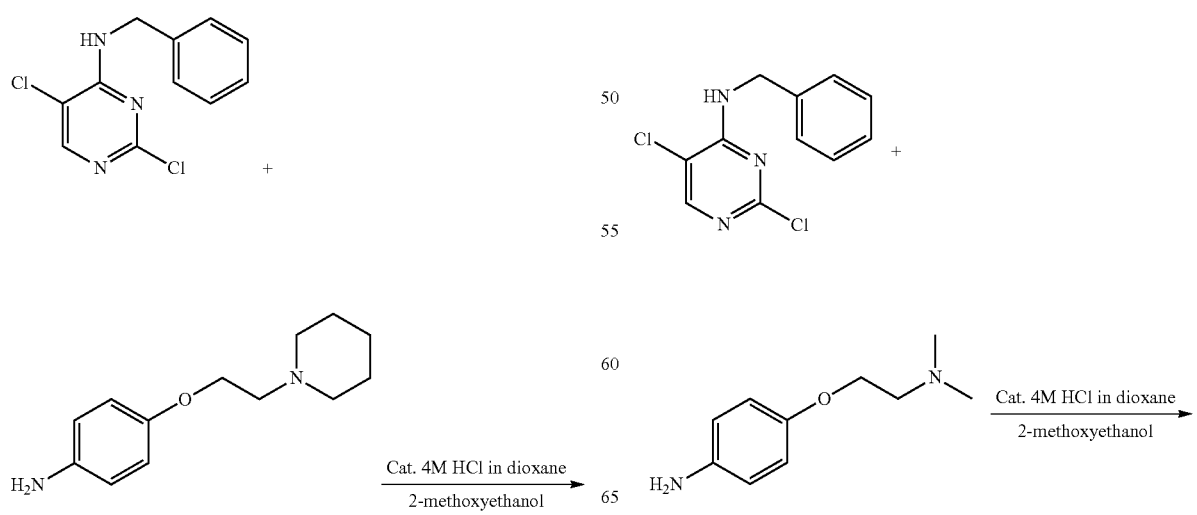

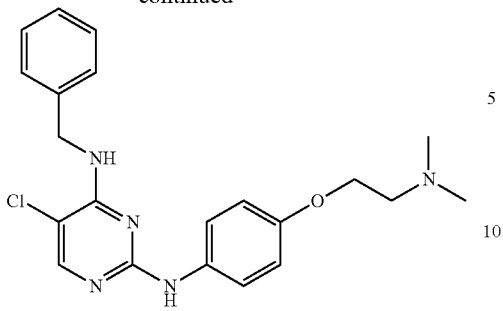

2,5-dichloro-4-benzylmethylaminopyrimidine (0.1 g, 0.39 mmol) and 4-(2-(dimethylamino)ethoxy)aniline (71 mg, 0.39 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.079 g, 51%); $^1$H NMR (400 MHz, CDCl$_3$) δ 2.32 (s, 6H), 2.70 (t, J=5.76 Hz, 2H), 4.02 (t, J=5.8 Hz, 2H), 4.65 (d, J=5.72 Hz, 2H), 5.58 (t, J=5.64 Hz, 1H), 6.82 (d, J=9 Hz, 2H), 7.28-7.36 (m, 7H), 7.42 (s, 1H), 7.89 (s, 1H); $^{13}$C NMR (400 MHz, CDCl$_3$) δ 44.84, 45.96, 58.41, 66.35, 104.16, 114.80, 121.45, 127.50, 127.52, 128.73, 133.09, 138.35, 153.27, 154.48, 157.75, 158.54.

Example 20. Preparation of Compound No. 20

Example 20-1. Preparation of 2-chloro-4-(furan-2-yl)methylamino-5-fluoropyrimidine

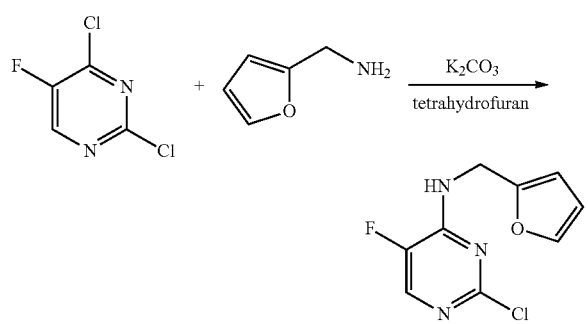

2,4-dichloro-5-fluoropyrimidine (2.0 g, 12 mmol) was added to a round bottom flask and dissolved in tetrahydrofuran (40 mL), and furfurylamine (1.15 mL, 12 mmol) and potassium carbonate (4.97 g, 36 mmol) were added thereto, followed by stirring at 60° C. for 24 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (2.17 g, 80%); $^1$H NMR (400 MHz, CDCl$_3$) δ 4.70 (d, J=5.52 Hz, 2H), 5.57 (s, 1H), 6.34-6.36 (m, 2H), 7.39 (s, 1H), 7.91 (d, J=2.68 Hz, 1H); $^{13}$C NMR (400 MHz, CDCl$_3$) δ 37.62, 108.47, 110.61, 139.90, 140.10, 142.68, 143.99, 146.54, 149.99, 153.15, 153.27, 154.61.

Example 20-2. Preparation of 4-(furan-2-yl)methylamino-5-fluoro-2-[4-{2-(pyrrolidin-1-yl)ethoxy}phenylamino]pyrimidine

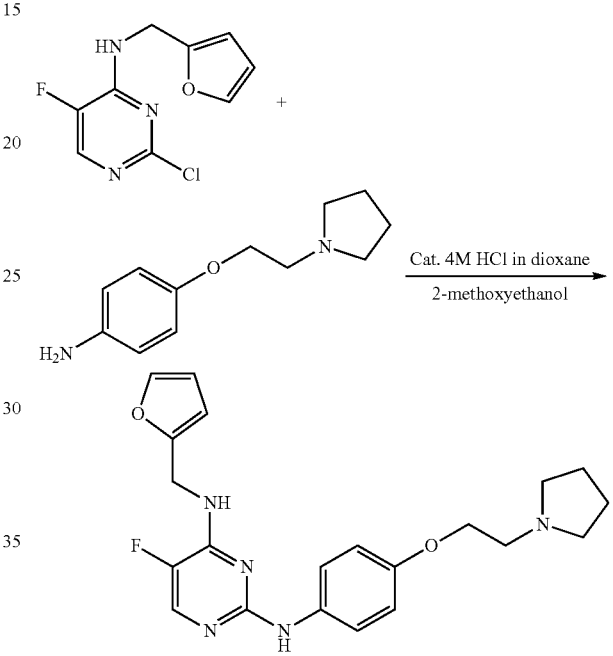

2-chloro-4-(furan-2-yl)methylamino-5-fluoropyrimidine (0.1 g, 0.44 mmol) and 4-(2-(pyrrolidin-1-yl)ethoxy)aniline (83 μL, 0.44 mmol) were dissolved in 2-methoxyethanol (9 mL) in a round bottom flask, and hydrochloric acid (0.056 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 63%); $^1$H NMR (400 MHz, CDCl$_3$) δ 1.79-1.82 (m, 4H), 2.60-2.63 (m, 4H), 2.89 (t, J=6.04 Hz, 2H), 4.09 (t, J=6.08 Hz, 2H), 4.65 (d, J=5.6 Hz, 2H), 5.26 (s, 1H), 6.25 (d, J=3.16 Hz, 1H), 6.33-6.34 (m, 1H), 6.88 (d, J=8.96 Hz, 3H), 7.38 (s, 1H), 7.42 (d, J=8.96 Hz, 2H), 7.78 (d, J=3.24 Hz, 1H); $^{13}$C NMR (400 MHz, CDCl$_3$) δ 23.50, 37.45, 54.72, 55.19, 67.48, 107.59, 110.48, 114.89, 121.15, 133.39, 139.25, 139.44, 140.06, 142.30, 142.48, 151.37, 152.07, 152.19, 154.43, 156.17, 156.20.

Example 21. Preparation of Compound No. 21

Example 21-1. Preparation of 4-chloro-5-trifluoromethyl-2-[4-{2-(pyrrolidin-1-yl)ethoxy}phenylamino]pyrimidine

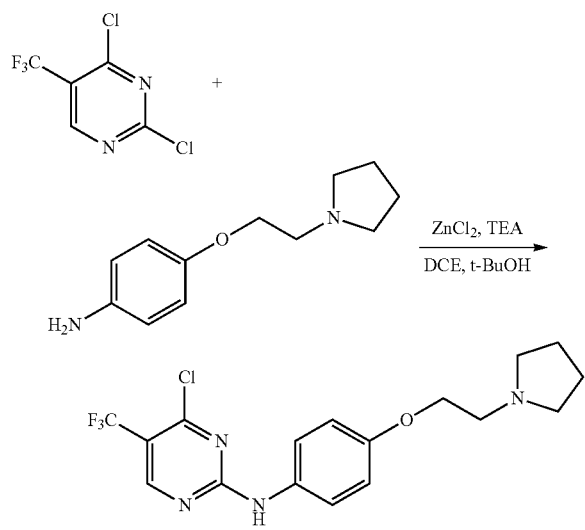

2,4-dichloro-5-trifluoromethylpyrimidine (1.0 g, 4.61 mmol) was added to a round bottom flask and was dissolved in a solution of tert-butanol and dichloroethane (1:1, 40 mL) and then stirred in zinc chloride (5.53 mL, 1 M solution in ether) at 0° C. After one hour, 4-(2-(pyrrolidin-1-yl)ethoxy)aniline (0.87 mL, 4.61 mmol) and triethylamine (0.71 mL, 5.07 mmol) were added to the reaction solution. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (methanol:dichloromethane, 2:3, v/v) to obtain a compound (35 mg, 2%); $^1$H NMR (400 MHz, CDCl$_3$) δ 1.81 (s, 5H), 2.65 (s, 5H), 2.92 (t, J=5.92 Hz, 2H), 3.92 (s, 1H), 4.11 (t, J=5.92 Hz, 2H), 6.92 (d, J=9.0 Hz, 2H), 7.43 (d, J=8.8 Hz, 2H), 8.50 (s, 1H); $^{13}$C NMR (400 MHz, CDCl$_3$) (23.48, 54.72, 55.07, 67.34, 114.57, 114.83, 115.04, 121.34, 122.93, 124.54, 130.30, 156.18, 157.35, 160.91.

Example 21-2. Preparation of 4-(furan-2-yl)methylamino-5-trifluoromethyl-2-[4-{2-(pyrrolidin-1-yl)ethoxy}phenylamino]pyrimidine

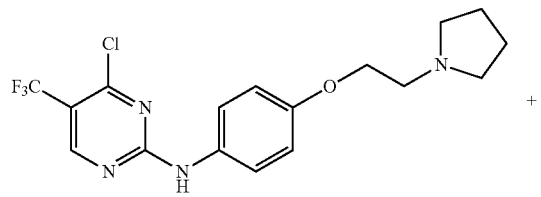

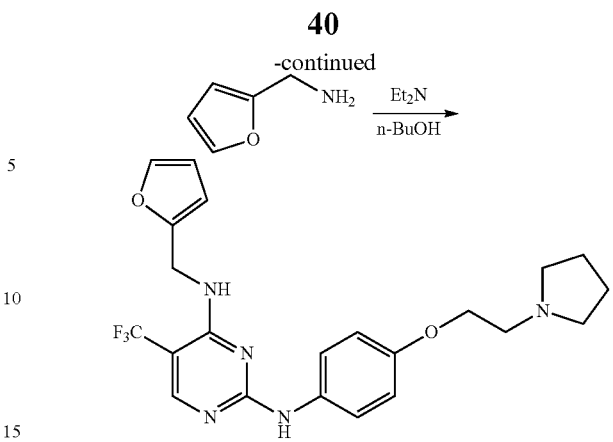

4-chloro-5-trifluoromethyl-2-[4-{2-(pyrrolidin-1-yl)ethoxy}phenylamino]pyrimidine (35 mg, 0.09 mmol) was added to a round bottom flask and then dissolved in 1-butanol (5 mL), and furfurylamine (8 μL, 0.09 mmol) and triethylamine (38 μL, 0.27 mmol) were added thereto, followed by stirring at 80° C. for 16 hours. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (12 mg, 29%); $^1$H NMR (400 MHz, CDCl$_3$) δ 1.79-1.82 (m, 4H), 2.61-2.64 (m, 4H), 2.90 (t, J=5.96 Hz, 2H), 4.10 (t, J=6.04 Hz, 2H), 4.68 (d, J=5.36 Hz, 2H), 5.43 (s, 1H), 6.21 (d, J=2.84 Hz, 1H), 6.33-6.34 (m, 1H), 6.90 (d, J=9.0 Hz, 2H), 7.19 (s, 1H), 7.39 (d, J=1.04 Hz, 1H), 7.41 (s, 1H), 7.43 (s, 1H), 8.16 (s, 1H); $^{13}$C NMR (400 MHz, CDCl$_3$) δ 23.51, 38.01, 54.74, 55.16, 67.47, 107.45, 110.45, 114.85, 122.32, 123.62, 124.56, 126.30, 131.91, 142.33, 151.15, 155.11, 155.16, 155.26, 158.59, 161.17.

Example 22. Preparation of Compound No. 22

Example 22-1. Preparation of 2-chloro-4-(furan-2-yl)methylaminoquinazoline

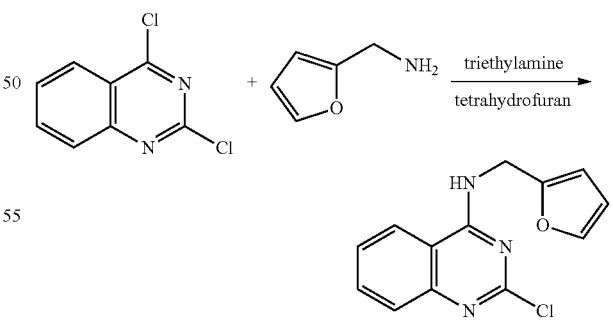

2,4-dichloroquinazoline (1.0 g, 5.02 mmol) was added to a round bottom flask and dissolved in tetrahydrofuran (40 mL), and then furfurylamine (0.46 mL, 5.02 mmol) and triethylamine (2.10 mL, 15.07 mmol) were added thereto, followed by stirring at 60° C. for 1 hour. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (1.15 g, 88%); $^1$H NMR (400 MHz, CDCl$_3$) δ 4.86 (d, J=5.16 Hz, 2H), 6.23 (s, 1H), 6.36-6.39 (m, 2H), 7.40-7.40 (d, J=0.96 Hz, 1H), 7.43-7.47 (m, 1H), 7.69-7.78 (m, 3H); $^{13}$C NMR (400 MHz, CDCl$_3$) δ 38.49, 108.64, 110.68, 113.17, 120.80, 126.30, 127.91, 133.62, 142.62, 150.24, 150.93, 157.54, 160.48.

Example 22-2. Preparation of 4-(furan-2-yl)methyl-amino-2-[4-{2-(pyrrolidin-1-yl)ethoxy}phenylamino]quinazoline

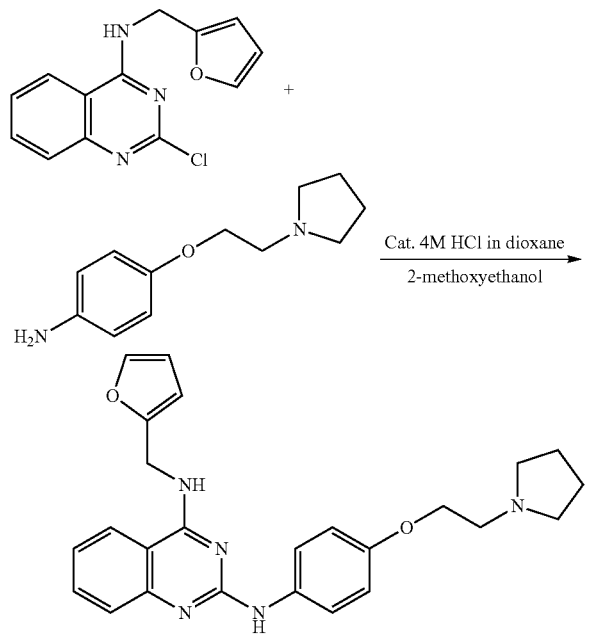

2-chloro-4-(furan-2-yl)methylaminoquinazoline (0.1 g, 0.39 mmol) and 4-(2-(pyrrolidin-1-yl)ethoxy)aniline (0.08 g, 0.39 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (97 mg, 59%); $^1$H NMR (400 MHz, CDCl$_3$) δ 1.77 (s, 4H), 2.59 (s, 4H), 2.86 (t, J=6 Hz, 2H), 4.06 (t, J=6.0 Hz, 2H), 4.73 (d, J=5.12 Hz, 2H), 5.24 (s, 1H), 6.20-6.22 (m, 2H), 6.28-6.29 (m, 1H), 6.85 (d, J=8.96 Hz, 2H), 7.02-7.06 (m, 1H), 7.27 (s, 1H), 7.33 (d, J=1 Hz, 1H), 7.50 (s, 3H), 7.55 (d, J=8.92 Hz, 2H); $^{13}$C NMR (400 MHz, CDCl$_3$) δ 23.51, 38.17, 54.71, 55.21, 67.44, 107.69, 110.55, 111.48, 114.83, 121.05, 121.35, 121.73, 126.05, 132.78, 133.70, 142.16, 151.63, 151.76, 154.24, 157.20, 159.92.

Example 23. Preparation of Compound No. 23

Example 23-1. Preparation of 2-chloro-4-(furan-2-yl)methylamino-5,6,7,8-tetrahydroquinazoline

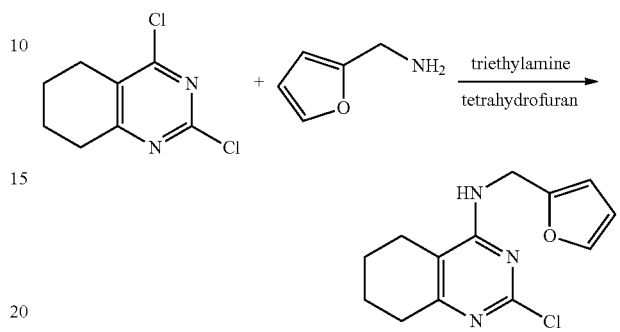

2,4-dichloro-5,6,7,8-tetrahydroquinazoline (0.5 g, 2.46 mmol) was added to a round bottom flask and dissolved in tetrahydrofuran (30 mL), and furfurylamine (0.23 mL, 2.46 mmol) and triethylamine (1.03 mL, 7.39 mmol) were added thereto, followed by stirring at 60° C. for 1 hour. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.22 g, 34%); $^1$H NMR (400 MHz, CDCl$_3$) δ 1.82 (s, 4H), 2.28 (s, 2H), 2.68 (s, 2H), 4.68 (d, J=4.8 Hz, 2H), 4.99 (s, 1H), 6.32 (d, J=12.4 Hz, 2H), 7.37 (s, 1H); $^{13}$C NMR (400 MHz, CDCl$_3$) δ 21.82, 21.86, 21.91, 31.63, 38.20, 108.01, 110.53, 110.55, 142.37, 151.08, 157.37, 161.42, 164.43.

Example 23-2. Preparation of 4-(furan-2-yl)methyl-amino-2-[4-{2-(pyrrolidin-1-yl)ethoxy} phenylamino]-5,6,7,8-tetrahydroquinazoline

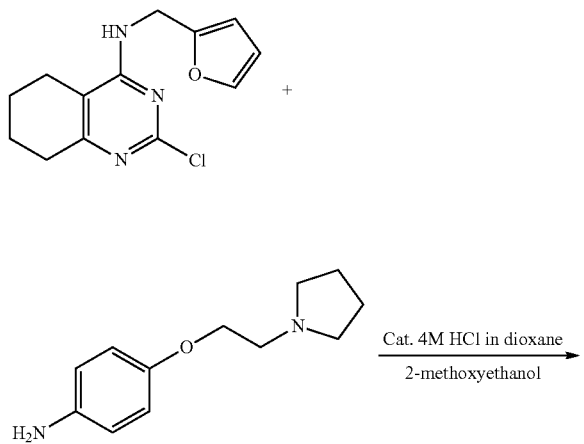

-continued

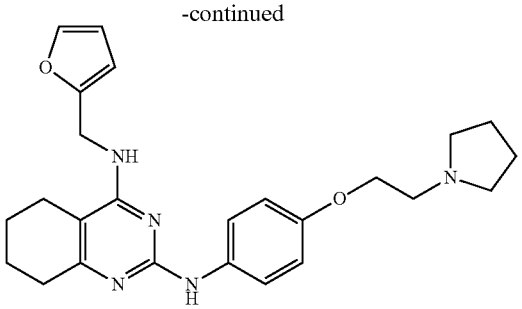

2-chloro-4-(furan-2-yl)methylamino-5,6,7,8-tetrahydroquinazoline (0.1 g, 0.38 mmol) and 4-(2-(pyrrolidin-1-yl)ethoxy)aniline (78 mg, 0.379 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.06 g, 37%); $^1$H NMR (400 MHz, CDCl$_3$) δ 1.77-1.81 (m, 8H), 2.24 (t, J=4.88 Hz, 2H), 2.56-2.62 (m, 6H), 2.87 (t, J=12.08 Hz, 2H), 4.08 (t, J=6.08 Hz, 2H), 4.65 (d, J=5.4 Hz, 2H), 4.79 (t, J=5.36 Hz, 1H), 6.21 (d, J=3.16 Hz, 1H), 6.30-6.31 (m, 1H), 6.85 (d, J=9.08 Hz, 3H), 7.36 (d, J=1 Hz, 1H), 7.48 (d, J=8.96 Hz, 2H); $^{13}$C NMR (400 MHz, CDCl$_3$) δ 21.81, 22.41, 22.59, 23.51, 31.92, 38.15, 54.71, 55.22, 67.51, 103.29, 107.15, 110.43, 114.80, 120.41, 134.22, 141.95, 152.48, 153.74, 157.65, 160.62, 162.66.

Example 24. Preparation of Compound No. 24

Example 24-1. Preparation of 2-chloro-4-(furan-2-yl)methylamino-6,7-dihydro-5H-cyclopenta[d]pyrimidine

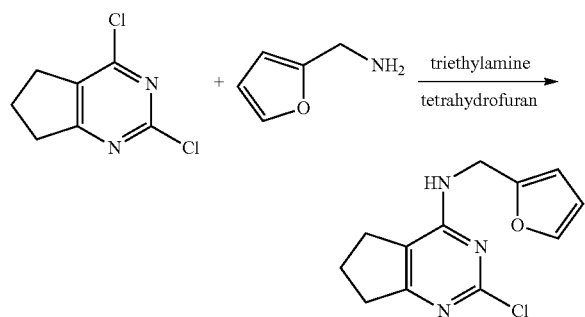

2,4-dichloro-6,7-dihydro-5H-cyclopenta[d]pyrimidine (0.5 g, 2.64 mmol) was added to a round bottom flask and dissolved in tetrahydrofuran (30 mL), and then furfurylamine (0.24 mL, 2.64 mmol) and triethylamine (1.11 mL, 7.93 mmol) were added thereto, followed by stirring at 60° C. for 1 hour. After completion of the reaction, the solvent was removed by distillation under reduced pressure and water was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.32 g, 48%); $^1$H NMR (400 MHz, CDCl$_3$) δ 2.07-2.15 (m, 2H), 2.63 (t, J=7.36 Hz, 2H), 2.84 (t, J=7.72 Hz, 2H), 4.68 (d, J=5.48 Hz, 2H), 5.10 (s, 1H), 6.29 (d, J=3.04 Hz, 1H), 6.32-6.33 (m, 1H), 7.36 (d, J=1 Hz, 1H); $^{13}$C NMR (400 MHz, CDCl$_3$) δ 21.60, 26.19, 33.85, 37.79, 107.98, 110.51, 114.89, 142.30, 151.07, 159.01, 159.51, 173.43.

Example 24-2. Preparation of 4-(furan-2-yl)methylamino-2-[4-{2-(pyrrolidin-1-yl)ethoxy} phenylamino]-6,7-dihydro-5H-cyclopenta[d]pyrimidine

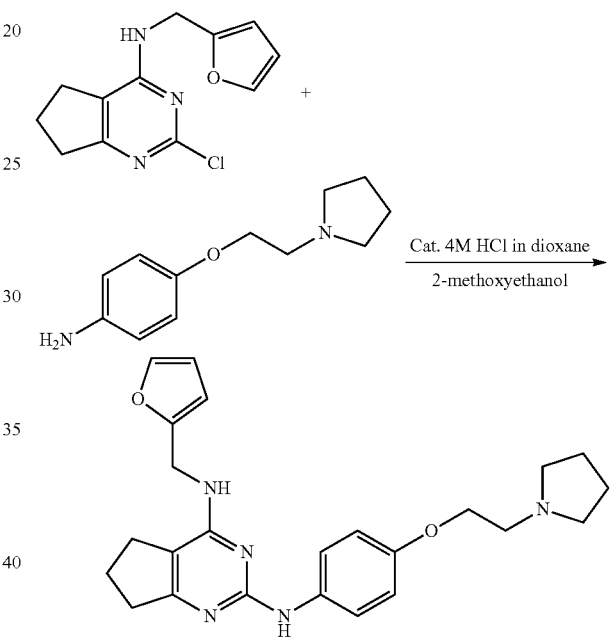

2-chloro-4-(furan-2-yl)methylamino-6,7-dihydro-5H-cyclopenta[d]pyrimidine (0.1 g, 0.4 mmol) and 4-(2-(pyrrolidin-1-yl)ethoxy)aniline (83 mg, 0.4 mmol) were dissolved in 2-methoxyethanol (9 mL) and then hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.1 g, 60%); $^1$H NMR (400 MHz, CDCl$_3$) δ 1.79 (s, 4H), 2.02-2.07 (m, 2H), 2.56 (t, J=7.08 Hz, 2H), 2.62 (s, 4H), 2.75 (t, J=7.48 Hz, 2H), 2.88 (t, J=5.96 Hz, 2H), 4.08 (t, J=5.92 Hz, 2H), 4.66 (d, J=5.52 Hz, 2H), 4.76 (s, 1H), 6.22 (s, 1H), 6.31 (s, 1H), 6.85 (d, J=8.48 Hz, 2H), 7.20 (d, J=14.04 Hz, 1H), 7.36 (s, 1H), 7.49 (d, J=8.8 Hz, 2H); $^{13}$C NMR (400 MHz, CDCl$_3$) δ 21.75, 23.49, 26.23, 34.06, 37.81, 54.69, 55.18, 67.44, 107.02, 107.21, 110.44, 114.78, 120.74, 134.04, 142.00, 152.37, 153.90, 158.86, 159.73, 171.83.

Example 25. Preparation of Compound No. 25

Example 25-1. Preparation of 2-chloro-4-((S)-tetrahydrofuran-2-yl)methylamino-5-methylpyrimidine

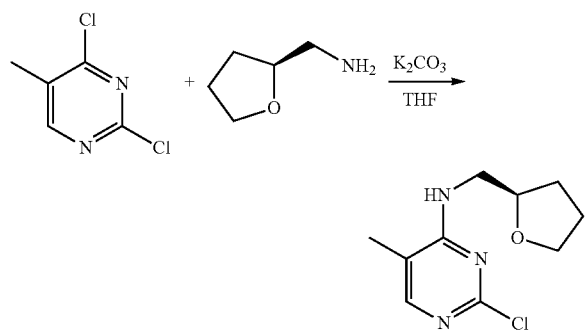

2,4-dichloro-5-methylpyrimidine (0.35 g, 2.15 mmol) was added to a round bottom flask and dissolved in tetrahydrofuran (20 mL), and then (S)-tetrahydrofurfurylamine (0.22 g, 2.15 mmol) and potassium carbonate (0.9 g, 6.44 mmol) were added thereto, followed by stirring at 60° C. for 24 hours. After completion of the reaction, the reaction solution was allowed to cool to room temperature and then filtered. The solvent was removed from the filtrate by distillation under reduced pressure and a saturated aqueous sodium chloride solution was added to the reaction mixture. The resulting mixture was extracted with dichloromethane and dried over anhydrous magnesium sulfate. The solvent was removed by distillation under reduced pressure and the residue was purified by column chromatography (ethyl acetate:hexane, 1:1, v/v) to obtain a compound (0.36 g, 73%); $^1$H NMR (400 MHz, CDCl$_3$) δ 1.56-1.64 (m, 1H), 1.90-1.97 (m, 2H), 2.00 (s, 3H), 2.03-2.08 (m, 1H), 3.31-3.37 (m, 1H), 3.75-3.91 (m, 3H), 4.08-4.14 (m, 1H), 5.50 (s, 1H), 7.78 (s, 1H); $^{13}$C NMR (400 MHz, CDCl$_3$) δ 12.89, 25.77, 28.74, 44.78, 68.02, 77.14, 112.13, 154.50, 158.38, 162.25.

Example 25-2. Preparation of 4-((S)-tetrahydrofuran-2-yl)methylamino-5-methyl-2-[4-{2-(pyrrolidin-1-yl)ethoxy}phenylamino]pyrimidine

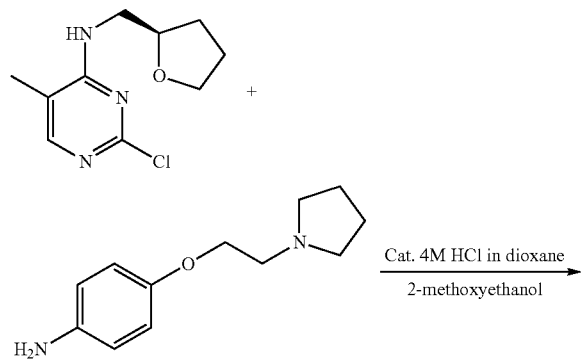

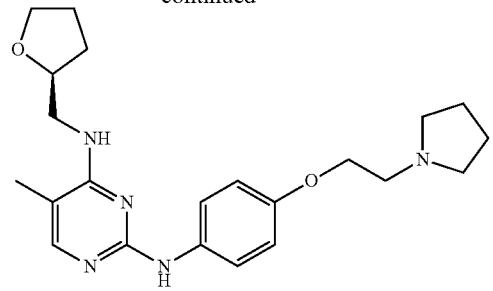

2-chloro-4-((S)-tetrahydrofuran-2-yl) methylamino-5-methylpyrimidine (0.1 g, 0.44 mmol) and 4-(2-(pyrrolidin-1-yl)ethoxy)aniline (0.09 g, 0.44 mmol) were dissolved in 2-methoxyethanol (9 mL), and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 63%); $^1$H NMR (400 MHz, CDCl$_3$) δ 1.55-1.63 (m, 1H), 1.77-1.81 (m, 4H), 1.86-1.93 (m, 5H), 1.95-2.03 (m, 1H), 2.59-2.62 (m, 4H), 2.87 (t, J=6.04 Hz, 2H), 3.33-3.40 (m, 1H), 3.74-3.83 (m, 2H), 3.85-3.90 (m, 1H), 4.08 (t, J=6.08 Hz, 2H), 4.11-4.15 (m, 1H), 5.05 (t, J=5.6 Hz, 1H), 6.86 (d, J=9.0 Hz, 2H), 7.47 (d, J=9.0 Hz, 2H), 7.53 (s, 1H), 7.69 (s, 1H); $^{13}$C NMR (400 MHz, CDCl$_3$) δ 13.00, 23.48, 25.90, 28.80, 44.70, 54.68, 55.19, 67.44, 68.09, 77.81, 104.16, 114.74, 120.77, 134.20, 153.79, 154.21, 159.15, 161.41.

Example 26. Preparation of Compound No. 26

Example 26-1. Preparation of 2,5-dichloro-4-((S)-tetrahydrofuran-2-yl)methylamino pyrimidine

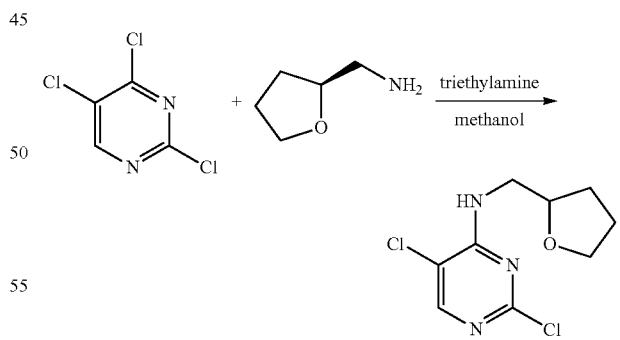

2,4,5-trichloropyrimidine (0.35 g, 1.91 mmol) was added to a round bottom flask and dissolved in methanol (20 mL), and then (S)-tetrahydrofurfurylamine (0.19 g, 1.91 mmol) and triethylamine (0.8 mL, 5.72 mmol) were added thereto, followed by stirring at 0° C. for 2 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (ethyl acetate:hexane, 1:1, v/v) to obtain a compound (0.38 g, 80%); $^1$H NMR (400 MHz, CDCl$_3$) δ 1.56-1.64 (m, 1H), 1.90-1.98 (m, 2H), 2.02-2.10 (m, 1H), 3.37-3.43 (m, 1H), 3.76-3.85 (m, 2H), 3.82-3.93 (m, 1H), 4.08-4.15 (m, 1H), 6.17 (s, 1H), 8.01 (s, 1H); $^{13}$C NMR (400 MHz, CDCl$_3$) δ 25.76, 28.71, 44.81, 68.09, 76.83, 113.19, 153.36, 158.20, 158.76.

Example 26-2. Preparation of 5-chloro-4-((S)-tetrahydrofuran-2-yl)methylamino-2-[4-{2-(pyrrolidin-1-yl)ethoxy}phenylamino]pyrimidine

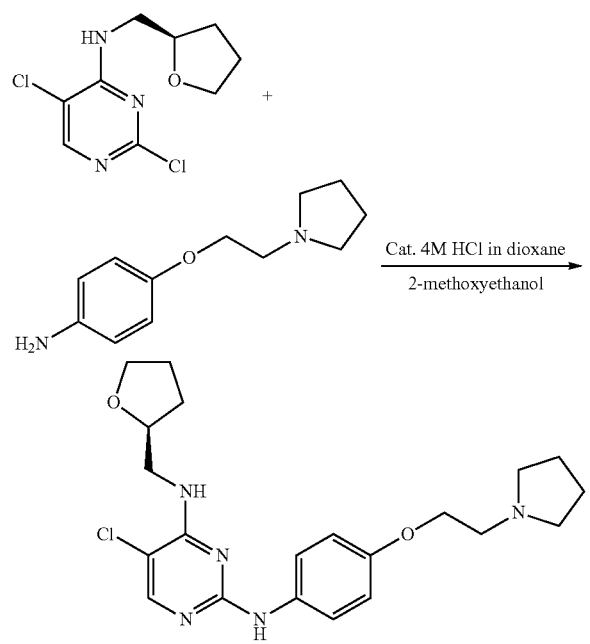

2,5-dichloro-4-((S)-tetrahydrofuran-2-yl)methylaminopyrimidine (0.1 g, 0.4 mmol) and 4-(2-(pyrrolidin-1-yl)ethoxy)aniline (83 mg, 0.4 mmol) were dissolved in 2-methoxyethanol (9 mL) in a round bottom flask, and hydrochloric acid (0.05 mL of a 4M dioxane solution) was added thereto, followed by stirring at 110° C. for 24 hours. After completion of the reaction, the solvent was removed by distillation under reduced pressure and a saturated aqueous sodium hydrogen carbonate solution was added to the reaction mixture. The resulting mixture was extracted with dichloromethane and dried over anhydrous magnesium sulfate, and the solvent was removed by distillation under reduced pressure. The residue was purified by column chromatography (methanol:dichloromethane, 2:3, v/v) to obtain a compound (0.11 g, 65%); $^1$H NMR (400 MHz, CDCl$_3$) δ 1.46-1.54 (m, 1H), 1.69-1.73 (m, 4H), 1.78-1.85 (m, 2H), 1.86-1.94 (m, 1H), 2.51-2.54 (m, 4H), 2.80 (t, J=6.0 Hz, 2H), 3.30-3.37 (m, 1H), 3.61-3.72 (m, 2H), 3.78-3.83 (m, 1H), 4.00 (t, J=5.96 Hz, 3H), 5.58 (t, J=5.60 Hz, 1H), 6.78 (d, J=9.0 Hz, 2H), 7.34 (d, J=8.96 Hz, 2H), 7.59 (s, 1H), 7.78 (s, 1H); $^{13}$C NMR (400 MHz, CDCl$_3$) δ 23.49, 25.90, 28.77, 44.59, 54.70, 55.16, 67.41, 68.22, 77.47, 104.25, 114.75, 121.39, 133.28, 153.03, 154.40, 157.94, 158.46.

TEST EXAMPLE

Representative compounds of the examples described above were subjected to the following tests.

Test Example 1. Measurement of Kinase Inhibitory Activity (1) Kinase Enzyme Screening Method Kinase screening was performed using a "HotSpot" assay platform method by Reaction Biology Corporation. The reaction buffer used herein contained 20 mM HEPES (pH 7.5), 10 mM MgCl$_2$, 1 mM EGTA, 0.02% Brij35, 0.02 mg/mL BSA, 0.1 mM Na$_3$VO$_4$, 2 mM DTT and 1% DMSO. The required cofactors were added in accordance with the kinase reaction. Freshly made buffer and cofactors were added at a concentration of 20 μM during the selected enzyme reaction. A solution of the test compound in dimethylsulfoxide (DMSO) was added at a suitable concentration to this solution. In order to initiate reaction, 339-ATP (specific activity 500 μCi/μL) was added and incubated at room temperature for 2 hours. The test compound was screened at a starting concentration of 20 μM in a 10-dose IC$_{50}$ mode. IC$_{50}$ of Staurosporine used as a control drug was obtained at a starting concentration of 20 μM in a 10-dose IC$_{50}$ mode. The reaction was carried out at an ATP concentration of 10 μM, and the results are summarized in the following Tables 1, 2 and 3.

(2) MV-4-11 Cell Screening Method

Compound 1 was dissolved in DMSO to prepare a 10 mM solution. A control compound was a 1 mM Staurosporine solution in DMSO. MV-4-11 cells were purchased from the American Type Culture Collection (Manassas, Va.) and cell culture media used herein were Iscove's DMEM mixed with 10% FBS and supplemented with 100 μg/mL penicillin and 100 μg/mL streptomycin, which were incubated at 37° C. in 5% CO$_2$ and 95% air under humid conditions.

Compound 1 was diluted in DMSO by 10-dose and 3-fold dilution methods at a starting concentration at 10 mM and loaded onto 384-well plates twice with 25 nL of staurosporine. 25 μL of culture media containing 2,000 MV-4-11 cells were added and incubated at 37° C. in the presence of 5% CO$_2$ for 72 hours. Then, the culture solution was mixed in an orbital shaker for 2 minutes and incubated at room temperature for 15 minutes. The luminescence is measured using an Envision 2104 Multilabel Reader (PerkinElmer, Santa Clara, Calif.) and viable cells present in the culture are measured according to the amount of ATP in the culture solution. IC$_{50}$ values are measured using the GraphPad Prism 4 program in accordance with the sigmoidal dose-response equation.

Table 1 shows activities against various kinases of representative compounds.

TABLE 1

| Kinase | Compound 1 (IC$_{50}$, nM) | Compound 5 (IC$_{50}$, nM) | Compound 20 (IC$_{50}$, nM) | Others |
|---|---|---|---|---|
| ACK1 | 38.8 | 51.3 | 101 | |
| ARK5/NUAK1 | 5.9 | 2.4 | 52.3 | |
| AXL | 443 | — | — | |
| AXL(R499C) | 207 | — | — | |
| c-MER | 14300 | — | — | |
| FLT3 | 10.3 | 2.87 | 22.0 | |
| JAK1 | 50.0 | 16.1 | 177 | |
| JAK2 | 50.1 | 8.85 | 99.1 | |
| JAK2(V617F) | 95.2 | 25.6 | 238 | |

TABLE 1-continued

| Kinase | Compound 1 (IC$_{50}$, nM) | Compound 5 (IC$_{50}$, nM) | Compound 20 (IC$_{50}$, nM) | Others |
|---|---|---|---|---|
| JAK3 | 207 | — | — | |
| LRRK2 | 113 | — | — | |
| mLK1/MAP3K9 | 148 | — | — | |
| PKCmu/PRKD1 | 167 | — | — | |
| RET | 488 | — | — | |
| SIK2 | 105 | — | — | |
| TYRO3/SKY | 10700 | — | — | |

—: Result is not measured

Table 2 shows FLT3-associated enzyme and cellular activity of representative compounds.

TABLE 2

| Test compound | FLT3 (IC$_{50}$, nM) | MV-4-11 cell line (IC$_{50}$, nM) | K-562 cell line (IC$_{50}$, μM) | FLT3-ITD (nM) | Ba/F3 GI$_{50}$ parental (μM) |
|---|---|---|---|---|---|
| Compound 1 | 10.3 | 65.9 | 5.1 | 92 | 1.79 |
| Compound 5 | 2.87 | — | — | 42 | 1.82 |
| Compound 20 | 22.0 | — | — | 178 | 6.67 |
| Compound 21 | — | — | — | 558 | 8.06 |
| Staurosporine | 1.2 | 0.087 | — | — | — |

—: Result is not measured

Table 3 shows results of FLT3 mutant enzyme activities of representative Compound 5.

TABLE 3

| Test compound | FLT3 (D835Y) (IC$_{50}$, nM) | FLT3 (ITD) (IC$_{50}$, nM) | FLT3 (ITD)-NPOS (IC$_{50}$, nM) |
|---|---|---|---|
| Compound 5 | <1 | 1.5 | 4.5 |

Test Example 2. Additional Screening Results Regarding Compound 5

(1) Cytotoxicity Test

Cell counting kit-8 assay is a general test method for identifying cell viability using a pale yellow tetrazolium salt called "WST-8". WST-8, which is soluble in water, is degraded by a dehydrogenase present in the cells, forming orange formazan. Formazan dye is formed by dehydrogenase activity proportional to the number of viable cells, and thus can be used as an indicator for cell viability. The Hill equation of Graphpad Prism was used for analysis. In Table 4, Compound 5 has an IC$_{50}$ of 10 μM or more as a criterion in respective cells, indicating that Compound 5 is not cytotoxic.

Table 4 shows the cytotoxicity results of Compound 5.

TABLE 4

| Compound | IC$_{50}$ (μM) | | | | |
|---|---|---|---|---|---|
| | VERO | HFL-1 | L929 | NIH3T3 | CHO-K1 |
| Compound 5 | 19.7 | 35.6 | 40.3 | >100 | >100 |

VERO: African green monkey kidney cell line, HFL-1: human embryonic lung cell line, L929: NCTC clone 929, mouse fibroblast cell line, NIH 3T3: mouse embryonic fibroblast cell line, CHO-K1: Chinese hamster ovary cell line.

(2) hERG K+ Channel Binding Assay

The hERG tracer and membranes were dissolved at room temperature before use, the tracer and hERG assay buffer were diluted at 1:62.5 and a test substance was diluted to 40 μM with assay buffer. 5 μL of the test substance, a positive control (astemizole or E-4031) and a negative control (DMSO) were dispensed into a 384-well plate, the membranes are dispensed at 10 μL using a multi-pipette and 5 μl of the tracer was dispensed. The light was blocked and incubated at 25° C. for 2 to 3 hours. Then, polarization was measured using a TECAN plate reader (Infinite M1000 pro).

As can be seen from Table 5 showing the results of the hERG K+ channel binding used as an indicator of toxicity in the heart, Compound 5 was stable in the heart.

Table 5 shows results of hERG K+ channel binding assay.

TABLE 5

| Compound | Concentration (μM) | IC$_{50}$ (μM) |
|---|---|---|
| Compound 5 | 0.01, 0.1, 1, 2, 5, 10, 20, 50 | 15.2 |

(3) CYP450 Assay

Compound 5 and a positive control stock solution were diluted with water to prepare a 40 μM working solution, and a solution containing an enzyme and a substrate was prepared using water and buffer. Compound 5/control/positive control and the solution were each dispensed on a 96-well and preincubated at 37° C. for 10 minutes. The resulting substance was reacted with NADPH for 20 minutes at 37° C. and a detection reagent was added to terminate the reaction. After stabilization at room temperature for 20 minutes, a luminescence signal was measured.

Table 6 shows inhibitory activity of Compound 5 against human CYP isozymes.

TABLE 6

| Compound (10 μM) | 1A2 | 2C9 | 2C19 | 2D6 | 3A4 |
|---|---|---|---|---|---|
| Compound 5 | 1.93 | <1 | 15.9 | 14.4 | 22.1 |
| Control compound* | 97.7 | 93.8 | 88.0 | 96.4 | 98.7 |

*1A2: αα-naphthoflavone (10 μM), 2C9: sulfaphenazole (10 μM), 2C19: amitriptyline (100 μM), 2D6: quinidine (10 μM), 3A4: ketoconazole (10 μM).

The results of Table 6 show that a substance that inhibits more than 50% of CYP enzyme activity was predicted to need attention. However, the results indicate that Compound 5 is stable.

These results showed that various pyrimidine compounds exhibited excellent activity against 5 to 6 kinases, which indicates the highest enzymatic activity in the world on ARK5/NUAK1 kinase (Compound 5: IC$_{50}$=2.4 nM, and Comparative Compound WZ4003 (IC$_{50}$=20 nM, HTH-01-015: IC$_{50}$=100 nM) and exhibited similar or superior activity to competing compounds such as Fedratinib and Quizartinib on ACK1, FLT3, JAK1, JAK2, JAK2 (V617F) and JAK3.

FORMULATION EXAMPLE

Meanwhile, the novel compound represented by Formula 1 according to the present invention can be formulated into various forms according to purpose. Some formulation methods include incorporation of the compound represented by Formula 1 according to the present invention as an active ingredient, but the present invention is not limited thereto.

Formulation Example 1. Tablet (Direct Pressurization)

5.0 mg of the active ingredient was sieved and 14.1 mg of lactose, 0.8 mg of crospovidone USNF and 0.1 mg of magnesium stearate were mixed and pressurized into tablets.

Formulation Example 2. Tablet (Wet Granulation)

5.0 mg of the active ingredient was sieved and was mixed with 16.0 mg of lactose and 4.0 mg of starch. 0.3 mg of Polysorbate 80 was dissolved in pure water, and an appropriate amount of the resulting solution was added to the resulting mixture, followed by granulation. The granules were dried, sieved and mixed with 2.7 mg of colloidal silicon dioxide and 2.0 mg of magnesium stearate. The granules were pressed into tablets.

Formulation Example 3. Powders and Capsules 5.0 mg of the active ingredient was sieved and then were mixed with 14.8 mg of lactose, 10.0 mg of polyvinylpyrrolidone and 0.2 mg of magnesium stearate. Hard No. 5 gelatin capsules were filled with the resulting mixture.

Formulation Example 4. Injection

Injections were prepared by incorporating 100 mg of the active ingredient as well as 180 mg of mannitol, 26 mg of $Na_2HPO_4/H_2O$ and 2,974 mg of distilled water.

As apparent from the fore-going, the novel pyrimidine derivative compound having various substituents represented by Formula 1, a solvate thereof or a pharmaceutically acceptable salt thereof according to one aspect of the present invention has excellent inhibitory activities on a variety of kinases.

The pyrimidine derivative compound having various substituents represented by Formula 1, a solvate thereof or a pharmaceutically acceptable salt thereof according to one aspect of the present invention has excellent inhibitory activities against at least one kinase enzyme of ARK5/NUAK1, ACK1, FLT3, JAK1, JAK2 and JAK2 (V617F).

The novel pyrimidine derivative compound having various substituents represented by Formula 1, a solvate thereof or a pharmaceutically acceptable salt thereof according to one aspect of the present invention is useful as a novel target therapeutic capable of treating various cancer diseases.

The pyrimidine derivative compound having various substituents represented by Formula 1 according to one aspect of the present invention, a solvate thereof or a pharmaceutically acceptable salt thereof may be used for treating, preventing or palliating leukemia, ovarian cancer, breast cancer, non-small cell carcinoma, colorectal cancer, glioma, and brain protein abnormalities such as Alzheimer's disease, progressive supranuclear palsy and frontotemporal dementia, that is, degenerative diseases caused by Tau deposition.

Hereinbelow, although embodiments of the present invention have been described with reference to the drawings, it will be obvious to those skilled in the art that the embodiments can be implemented in other specific forms without changing technical concepts or essential features of the present invention. Therefore, it should be construed that the aforementioned embodiments are illustrative and not restrictive in all respects.

What is claimed is:

1. A novel pyrimidine derivative compound represented by the following Formula 1, a stereoisomer thereof, a solvate thereof, or a pharmaceutically acceptable salt thereof:

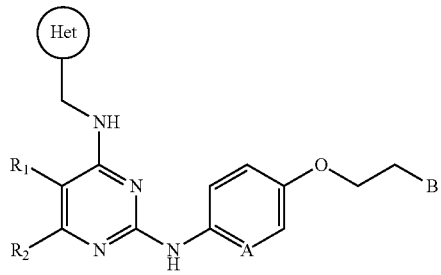

[Formula 1]

wherein

R1 and R2 are each independently a hydrogen atom, a halogen atom, a C1-C6 alkyl group, a C1-C6 haloalkyl group, —O—(C1-C6 alkyl), —O—(C1-C6 haloalkyl), —C(O)—(C1-C6 alkyl), —C(O)—O—(C1-C6 alkyl) or —O—C(O)—(C1-C6 alkyl), or R1 and R2 are bonded together to form a 5-membered to 6-membered saturated or unsaturated ring, or R1 and R2 are bonded together to form a 5-membered to 6-membered saturated or unsaturated heteroring including one to four heteroatoms selected from nitrogen (N) and oxygen (O) atoms;

Het is a C6-C15 aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms;

A is a carbon (C) or nitrogen (N) atom; and

B is a C6-C15 aryl group, a 5-membered to 14-membered heteraryl group including one to four heteroatoms selected from nitrogen (N), oxygen (O) and sulfur (S) atoms, or a 5-membered to 6-membered heterocyclic group including one or two heteroatoms selected from nitrogen (N) and oxygen (O) atoms.

2. The compound, a stereoisomer thereof, a solvate thereof, or a pharmaceutically acceptable salt thereof according to claim 1, wherein R1 and R2 are each independently a hydrogen atom, methyl, ethyl, CF3, F, Cl or Br, or R1 and R2 are bonded together to form a 5-membered to 6-membered saturated or unsaturated ring, or R1 and R2 are bonded together to form a 5-membered to 6-membered saturated or unsaturated heteroring including one to four heteroatoms selected from nitrogen (N) and oxygen (O) atoms;

Het represents a tetrahydrofuranyl group, a furanyl group, a pyranyl group, a pyridinyl group or a phenyl group; and B represents a pyrrolidinyl group, a piperidinyl group, a morpholinyl group, a piperazinyl group or an amino group.

3. The compound, a stereoisomer thereof, a solvate thereof, or a pharmaceutically acceptable salt thereof according to claim 1, wherein R1 and R2 are each independently a hydrogen atom, methyl, CF3, F or Cl, or R1 and R2 are bonded together to form a 6-membered unsaturated ring, or R1 and R2 are bonded together to form a 6-membered saturated ring, or R1 and R2 are bonded together to form a 5-membered saturated ring;

Het represents a tetrahydrofuranyl group, a furanyl group or a phenyl group; and B represents a pyrrolidinyl group, a piperidinyl group, or a dimethylamino group.

4. The compound, a stereoisomer thereof, a solvate thereof, or a pharmaceutically acceptable salt thereof according to claim 1, wherein the compound is selected from the following compounds:

(Compound No. 1) 4-(furan-2-yl)methylamino-5-methyl-2-[4-{2-(pyrrolidin-1-yl) ethoxy}phenylamino]pyrimidine;

(Compound No. 2) 4-(furan-2-yl)methylamino-5-methyl-2-[4-{2-(piperidin-1-yl) ethoxy}phenylamino]pyrimidine;

(Compound No. 3) 4-(furan-2-yl)methylamino-5-methyl-2-[4-{2-(dimethylamino)ethoxy}phenylamino]pyrimidine;

(Compound No. 4) 4-(furan-2-yl)methylamino-5-methyl-2-[2-amino-5-{2-(pyrrolidin-1-yl)ethoxy}pyridine]pyrimidine;

(Compound No. 5) 5-chloro-4-(furan-2-yl)methylamino-2-[4-{2-(pyrrolidin-1-yl) ethoxy}phenylamino]pyrimidine;

(Compound No. 6) 5-chloro-4-(furan-2-yl)methylamino-2-[4-{2-(piperidin-1-yl) ethoxy}phenylamino]pyrimidine;

(Compound No. 7) 5-chloro-4-(furan-2-yl)methylamino-2-[4-{2-(dimethylamino)ethoxy}phenylamino]pyrimidine;

(Compound No. 8) 4-(tetrahydrofuran-2-yl)methylamino-5-methyl-2-[4-{2-(pyrrolidin-1-Methoxy}phenylamino]pyrimidine;

(Compound No. 9) 4-(tetrahydrofuran-2-yl)methylamino-5-methyl-2-[4-{2-(piperidin-1-yl) ethoxy}phenylamino]pyrimidine;

(Compound No. 10) 4-(tetrahydrofuran-2-yl)methylamino-5-methyl-2-[4-{2-(dimethylamino) ethoxy}phenylamino]pyrimidine;

(Compound No. 11) 5-chloro-4-(tetrahydrofuran-2-yl) methylamino-2-[4-{2-(pyrrolidin-1-Methoxy}phenylamino]pyrimidine;

(Compound No. 12) 5-chloro-4-(tetrahydrofuran-2-yl) methylamino-2-[4-{2-(piperidin-1-yl) ethoxy}phenylamino]pyrimidine;

(Compound No. 13) 5-chloro-4-(tetrahydrofuran-2-yl) methylamino-2-[4-{2-(dimethylamino) ethoxy}phenylamino]pyrimidine;

(Compound No. 14) 4-benzylmethylamino-5-methyl-2-[4-{2-(pyrrolidin-1-yl) ethoxy}phenylamino]pyrimidine;

(Compound No. 15) 4-benzylmethylamino-5-methyl-2-[4-{2-(piperidin-1-yl) ethoxy}phenylamino]pyrimidine;

(Compound No. 16) 4-benzylmethylamino-5-methyl-2-[4-{2-(dimethylamino) ethoxy}phenylamino]pyrimidine;

(Compound No. 17) 5-chloro-4-benzylmethylamino-2-[4-{2-(pyrrolidin-1-yl) ethoxy}phenylamino]pyrimidine;

(Compound No. 18) 5-chloro-4-benzylmethylamino-2-[4-{2-(piperidin-1-yl) ethoxy}phenylamino]pyrimidine;

(Compound No. 19) 5-chloro-4-benzylmethylamino-2-[4-{2-(dimethylamino) ethoxy}phenylamino]pyrimidine;

(Compound No. 20) 4-(furan-2-yl) methylamino-5-fluoro-2-[4-{2-(pyrrolidin-1-yl)ethoxy}phenylamino] pyrimidine;

(Compound No. 21) 4-(furan-2-yl) methylamino-5-trifluoromethyl-2-[4-{2-(pyrrolidin-1-Methoxy}phenylamino]pyrimidine;

(Compound No. 22) 4-(furan-2-yl)methylamino-2-[4-{2-(pyrrolidin-1-yl) ethoxy}phenylamino]quinazoline;

(Compound No. 23) 4-(furan-2-yl)methylamino-2-[4-{2-(pyrrolidin-1-yl) ethoxy}phenylamino]-5,6,7,8-tetrahydroquinazoline;

(Compound No. 24) 4-(furan-2-yl)methylamino-2-[4-{2-(pyrrolidin-1-yl) ethoxy}phenylamino]-6,7-dihydro-5H-cyclopenta[d]pyrimidine;

(Compound No. 25) 4-((S)-tetrahydrofuran-2-yl) methylamino-5-methyl-2-[4-{2-(pyrrolidin-1-yl] ethoxy}phenylamino]pyrimidine; and (Compound No. 26) 5-chloro-4-((S)-tetrahydrofuran-2-yl) methylamino-2-[4-{2-(pyrrolidin-1-yl] ethoxy}phenylamino]pyrimidine.

5. A pharmaceutical composition for treating, preventing or palliating cancer comprising, as an active ingredient, the compound according to claim 1.

6. A pharmaceutical composition for treating, preventing or palliating a degenerative brain disease comprising, as an active ingredient, the compound according to claim 1.

7. A pharmaceutical composition for treating, preventing or palliating an immunological disease comprising, as an active ingredient, the compound according to claim 1.

8. A pharmaceutical composition for treating, preventing or palliating an inflammatory disease comprising, as an active ingredient, the compound according to claim 1.

9. The pharmaceutical composition according to claim 5, wherein the cancer comprises one or more of ovarian cancer, non-small cell carcinoma, colorectal cancer, glioma, breast cancer, esophageal cancer, lung cancer, uterine cancer, pancreatic cancer, prostate cancer and blood cancer.

10. The pharmaceutical composition according to claim 6, wherein the degenerative brain disease comprises one or more of Alzheimer's disease, Parkinson's disease, Lewy body dementia and frontotemporal dementia.

11. A pharmaceutical composition for treating, preventing or palliating cancer comprising, as an active ingredient, the compound according to claim 2.

12. A pharmaceutical composition for treating, preventing or palliating cancer comprising, as an active ingredient, the compound according to claim 3.

13. A pharmaceutical composition for treating, preventing or palliating cancer comprising, as an active ingredient, the compound according to claim 4.

14. A pharmaceutical composition for treating, preventing or palliating a degenerative brain disease comprising, as an active ingredient, the compound according to claim 2.

15. A pharmaceutical composition for treating, preventing or palliating a degenerative brain disease comprising, as an active ingredient, the compound according to claim 3.

16. A pharmaceutical composition for treating, preventing or palliating a degenerative brain disease comprising, as an active ingredient, the compound according to claim 4.

17. A pharmaceutical composition for treating, preventing or palliating an immunological disease comprising, as an active ingredient, the compound according to claim 2.

18. A pharmaceutical composition for treating, preventing or palliating an immunological disease comprising, as an active ingredient, the compound according to claim 3.

19. A pharmaceutical composition for treating, preventing or palliating an immunological disease comprising, as an active ingredient, the compound according to claim 4.

20. A pharmaceutical composition for treating, preventing or palliating an inflammatory disease comprising, as an active ingredient, the compound according to claim 2.

* * * * *